United States Patent
Chin et al.

(10) Patent No.: US 9,862,926 B2
(45) Date of Patent: Jan. 9, 2018

(54) INHIBITION OF INNATE IMMUNE RESPONSE

(75) Inventors: Cynthia Chin, Madison, WI (US); Anthony D. Person, Madison, WI (US); Gary A. Dahl, Madison, WI (US)

(73) Assignee: CellScript, LLC., Madison, WI (US)

( * ) Notice: Subject to any disclaimer, the term of this patent is extended or adjusted under 35 U.S.C. 154(b) by 0 days.

(21) Appl. No.: 14/129,703

(22) PCT Filed: Jun. 27, 2012

(86) PCT No.: PCT/US2012/044418
§ 371 (c)(1),
(2), (4) Date: Apr. 2, 2014

(87) PCT Pub. No.: WO2013/003475
PCT Pub. Date: Jan. 3, 2013

(65) Prior Publication Data
US 2014/0227300 A1    Aug. 14, 2014

Related U.S. Application Data

(60) Provisional application No. 61/501,420, filed on Jun. 27, 2011.

(51) Int. Cl.
| | | |
|---|---|---|
| C12P 21/02 | (2006.01) | |
| C12N 5/078 | (2010.01) | |
| A61K 38/16 | (2006.01) | |
| C07K 14/705 | (2006.01) | |
| C07K 14/715 | (2006.01) | |
| A61K 31/7105 | (2006.01) | |
| A61K 38/17 | (2006.01) | |
| A61K 38/21 | (2006.01) | |
| C07K 14/005 | (2006.01) | |
| A61K 31/711 | (2006.01) | |
| C12N 5/077 | (2010.01) | |
| C12N 5/074 | (2010.01) | |
| A61K 48/00 | (2006.01) | |
| C07H 21/02 | (2006.01) | |
| C12P 19/34 | (2006.01) | |

(52) U.S. Cl.
CPC .......... *C12N 5/0634* (2013.01); *A61K 31/711* (2013.01); *A61K 31/7105* (2013.01); *A61K 38/162* (2013.01); *A61K 38/1774* (2013.01); *A61K 38/21* (2013.01); *C07K 14/005* (2013.01); *C07K 14/70503* (2013.01); *C07K 14/7156* (2013.01); *C12N 5/0658* (2013.01); *C12N 5/0696* (2013.01); *C12N 2710/20022* (2013.01); *C12N 2710/22022* (2013.01); *C12N 2710/24122* (2013.01); *C12N 2760/16122* (2013.01)

(58) Field of Classification Search
None
See application file for complete search history.

(56) References Cited

U.S. PATENT DOCUMENTS

| | | |
|---|---|---|
| 6,458,932 B1 | 10/2002 | Novick et al. |
| 2003/0138404 A1* | 7/2003 | Maroun ...................... 424/85.5 |
| 2010/0273220 A1 | 10/2010 | Yanik et al. |

FOREIGN PATENT DOCUMENTS

| | | |
|---|---|---|
| EP | 0679717 | 8/1999 |
| WO | WO 2013/003475 | 1/2013 |

OTHER PUBLICATIONS

Alexopoulou et al. (2001) Recognition of double-stranded RNA and activation of NF-kappaB by Toll-like receptor 3. Nature 413, 732-738.
Andrews-Pfannkoch et al. (2010). Hydroxyapatite-mediated separation of double-stranded DNA, single-stranded DNA, and RNA genomes from natural viral assemblages. Appl Environ Microbiol 76, 5039-5045.
Angel et al (2010). Innate immune suppression enables frequent transfection with Rna encoding reprogramming proteins. PLoS One 5, e11756.
Arsenio et al. (2008). Antagonizing activity of vaccinia virus E3L against human interferons in Huh7 cells. Virology, 377:124-132.
Barber, R. (1966). The chromatographic separation of ribonucleic acids. Biochim Biophys Acta 114, 422-424.
Barret et al. (2008). Development of TLR inhibitors for the treatment of autoimmune diseases. Immunol Rev, 223:271-283.
Beattie et al. (1991). Vaccinia virus-encoded eIF-2 alpha homolog abrogates the antiviral effect of interferon. Virology 183, 419-422.
Carroll et al. (1993). Recombinant vaccinia virus K3L gene product prevents activation of double-stranded RNA-dependent, initiation factor 2 alpha-specific protein kinase. J Biol Chem 268, 12837-12842.
Carter et al. (1985). Improved oligonucleotide site-directed mutagenesis using M13 vectors. Nucleic Acids Res 13, 4431-4443.
Cazenave, C., and Uhlenbeck, O.C. (1994). RNA template-directed RNA synthesis by T7 RNA polymerase. Proc Natl Acad Sci U S A 91, 6972-6976.
Chang et al. (1992). The E3L gene of vaccinia virus encodes an inhibitor of the interferon-induced, double-stranded RNA-dependent protein kinase. Proc Natl Acad Sci U S A 89, 4825-4829.
Clawson, G.A., and Smuckler, E.A. (1982). Increased amounts of double-stranded RNA in the cytoplasm of rat liver following treatment with carcinogens. Cancer Res 42, 3228-3231.

(Continued)

*Primary Examiner* — Nancy J Leith
(74) *Attorney, Agent, or Firm* — Casmir Jones, S.C.

(57) ABSTRACT

The present invention provides methods, kits, and compositions for reducing an innate immune system response in a human or animal cell, tissue or organism. One embodiment comprises: introducing an Agent mRNA comprising in vitro-synthesized mRNA encoding one or more proteins that affect the induction, activity or response of an innate immune response pathway; whereby, the innate immune response in the cell, tissue or organism is reduced compared to the innate immune response in the absence of the Agent mRNA. Other embodiments are methods, compositions and kits for using an Agent mRNA for treating a disease or medical condition in a human or animal that exhibits symptoms of an elevated innate immune system, or for reducing an innate immune response that is induced in a human or animal cell, tissue or organism by a Foreign Substance that is administered to the cell, tissue or organism.

10 Claims, 11 Drawing Sheets

(56) References Cited

OTHER PUBLICATIONS

Colamonici et al. (1995). Vaccinia virus B18R gene encodes a type I interferon-binding protein that blocks interferon alpha transmembrane signaling. J Biol Chem 270, 15974-15978.

Davies et al. (1992). The vaccinia virus K3L gene product potentiates translation by inhibiting double-stranded-RNA-activated protein kinase and phosphorylation of the alpha subunit of eukaryotic initiation factor 2. J Virol 66, 1943-1950.

Davies et al. (1993) The E3L and K3L vaccinia virus gene products stimulate translation through inhibition of the double-stranded RNA-dependent protein kinase by different mechanisms, J Virol, 67:1688-1692.

Davis et al. (1987). Expression of a single transfected cDNA converts fibroblasts to myoblasts. Cell 51, 987-1000.

Diebold et al. (2004). Innate antiviral responses by means of TLR7-mediated recognition of single-stranded RNA. Science 303, 1529-1531.

Easton et al. (2010). Rapid, nondenaturing RNA purification using weak anion-exchange fast performance liquid chromatography. RNA 16, 647-653.

Franklin, R.M. (1966). Purification and properties of the replicative intermediate of the RNA bacteriophage R17. Proc Natl Aced Sci U S A 55, 1504-1511.

Garcia et al. (2002). Anti-apoptotic and oncogenic properties of the dsRNA-binding protein of vaccinia virus, E3L, Oncogene, 21:8379-8387.

Garcia et al. (2007). The dsRNA protein kinase PKR: virus and cell control, Biochimie, 89:799-811.

Gjerde et al. (2009). RNA purification and analysis : sample preparation, extraction, chromatography (Weinheim, Wiley-VCH), TOC only, will provide specific passages upon examiner request, 6 pages.

Heil et al. (2004). Species-specific recognition of single-stranded RNA via toll-like receptor 7 and 8. Science 303, 1526-1529.

Hemmi et al. (2002). Small anti-viral compounds activate immune cells via the TLR7 MyD88-dependent signaling pathway. Nat Immunol 3, 196-200.

Hemmi et al. (2000). A Toll-like receptor recognizes bacterial DNA. Nature 408, 740-745.

Isaacs et al. (1957). Virus interference. I. The interferon. Proc R Soc Lond B Biol Sci 147, 258-267.

Judge, A., and MacLachlan, I. (2008). Overcoming the innate immune response to small interfering RNA. Hum Gene Ther 19, 111-124.

Kariko et al. (2004). mRNA is an endogenous ligand for Toll-like receptor 3. J Biol Chem 279, 12542-12550.

Kunkel, T.A. (1985). Rapid and efficient site-specific mutagenesis without phenotypic selection. Proc Natl Acad Sci U S A 82, 488-492.

Levraud et al. (2007). Identification of the zebrafish IFN receptor: implications for the origin of the vertebrate IFN system. J Immunol 178, 4385-4394.

Lewandowski et al. (1971). Separation of the infectious ribonucleic acid of potato spindle tuber virus from double-stranded ribonucleic acid of plant tissue extracts. J Virol 8, 809-812.

Marq et al. (2009). The double-stranded RNA binding domain of the vaccinia virus E3L protein inhibits both RNA- and DNA-induced activation of interferon beta, J Biol Chem., 284:25471-25478.

Mellits et al. (1990). Removal of double-stranded contaminants from RNA transcripts: synthesis of adenovirus VA RNAI from a T7 vector. Nucleic Acids Res 18, 5401-5406.

Muller et al. (1994). Functional role of type I and type II interferons in antiviral defense. Science 264, 1918-1921.

Nelson et al. (1993). Interferon consensus sequence-binding protein, a member of the interferon regulatory factor family, suppresses interferon-induced gene transcription. Mol Cell Biol 13, 588-599.

Pays, E. (1977). Characterization of double-stranded ribonucleic acid sequences present in the initial transcription products of rat liver chromatin. Biochem J 165, 237-245.

Rice et al. (2011). Roles of vaccinia virus genes E3L and K3L and host genes PKR and RNase L during intratracheal infection of C57BL/6 mice. J Virol 85, 550-567.

Schulz et al. (2005). Toll-like receptor 3 promotes cross-priming to virus-infected cells. Nature 433, 887-892.

Symons et al. (1995). Vaccinia virus encodes a soluble type I interferon receptor of novel structure and broad species specificity. Cell 81, 551-560.

Triana-Alonso et al. (1995). Self-coded 3'-extension of run-off transcripts produces aberrant products during in vitro transcription with T7 RNA polymerase. J Biol Chem 270, 6298-6307.

Valentine et al., (2010). Inhibition of the RNA polymerase III-mediated dsDNA-sensing pathway of innate immunity by vaccinia virus protein E3. J Gen Virol., 91:2221-2229.

Vallette et al. (1989). Construction of mutant and chimeric genes using the polymerase chain reaction. Nucleic Acids Res 17, 723-733.

Wang et al. (2004). Toll-like receptor 3 mediates West Nile virus entry into the brain causing lethal encephalitis. Nat Med 10, 1366-1373.

Warren et al. (2010). Highly efficient reprogramming to pluripotency and directed differentiation of human cells with synthetic modified mRNA. Cell Stem Cell 7, 618-630.

Wells et al. (1985). Cassette mutagenesis: an efficient method for generation of multiple mutations at defined sites. Gene 34, 315-323.

Xiang et al. (2002). Blockade of interferon induction and action by the E3L double-stranded RNA binding proteins of vaccinia virus. J Virol 76, 5251-5259.

Zelcer et al. (1981). The detection and characterization of viral-related double-stranded RNAs in tobacco mosaic virus-infected plants. Virology 113, 417-427.

International Search Report and Written Opinion for PCT/US2012/044418, dated Oct. 4, 2012, 20 pages.

* cited by examiner

B18R mRNA sequence (SEQ ID NO:2)

5' GGGCGAAUUGGGUACCGGGCCCCCCCUCGAGGUCGACGGUAUCGAUAAGCUUGCUUGUUCUU
UUUGCAGAAGCUCAGAAUAAACGCUCAACUUUGGCAGAUCUGAUUCGAGGCCACCAUGACGAUG
AAAAUGAUGGUACAUAUAUAUUUCGUAUCAUUAUUGUUAUUGCUAUUCCACAGUUACGCCAUAG
ACAUCGAAAAUGAAAUCACAGAAUUCUUCAAUAAAAUGAGAGAUACUCUACCAGCUAAAGACUC
UAAAUGGUUGAAUCCAGCAUGUAUGUUCGGAGGCACAAUGAAUGAUAUAGCCGCUCUAGGAGAG
CCAUUCAGCGCAAAGUGUCCUCCUAUUGAAGACAGUCUUUUAUCGCACAGAUAUAAAGACUAUG
UGGUUAAAUGGGAAAGGCUAGAAAAAAAUAGACGGCGACAGGUUUCUAAUAAACGUGUUAAACA
UGGUGAUUUAUGGAUAGCCAACUAUACAUCUAAAUUCAGUAACCGUAGGUAUUUGUGCACCGUA
ACUACAAAGAAUGGUGACUGUGUUCAGGGUAUAGUUAGAUCUCAUAUUAGAAAACCUCCUUCAU
GCAUUCCAAAAACAUAUGAACUAGGUACUCAUGAUAAGUAUGGCAUAGACUUAUACUGUGGAAU
UCUUUACGCAAAACAUUAUAAUAAUAUAACUUGGUAUAAAGAUAAUAAGGAAAUUAAUAUCGAC
GACAUUAAGUAUUCACAAACGGGAAAGGAAUUAAUUAUUCAUAAUCCAGAGUUAGAAGAUAGCG
GAAGAUACGACUGUUACGUUCAUUACGACGACGUUAGAAUCAAGAAUGAUAUCGUAGUAUCAAG
AUGUAAAAUACUUACGGUUAUACCGUCACAAGACCACAGGUUUAAACUAAUACUAGAUCCAAAA
AUCAACGUAACGAUAGGAGAACCUGCCAAUAUAACAUGCACUGCUGUGUCAACGUCAUUAUUGA
UUGACGAUGUACUGAUUGAAUGGGAAAAUCCAUCCGGAUGGCUUAUAGGAUUCGAUUUUGAUGU
AUACUCUGUUUUAACUAGUAGAGGCGGUAUUACCGAGGCGACCUUGUACUUUGAAAAUGUUACU
GAAGAAUAUAUAGGUAAUACAUAUAAAUGUCGUGGACACAACUAUUAUUUUGAAAAAACCCUUA
CAACUACAGUAGUAUUGGAGUAAAAGCUAUCACUAGUGACUGACUAGGAUCUGGUUACCACUAA
ACCAGCCUCAAGAACACCCGAAUGGAGUCUCUAAGCUACAUAAUACCAACUUACACUUUACAAA
AUGUUGUCCCCCAAAAUGUAGCCAUUCGUAUCUGCUCCUAAUAAAAAGAAAGUUUCUUCACAUU
CUGGAUCCACUAGUUCUAGAGCGGCC 3'

B.

B18R amino acid sequence (SEQ ID NO:3)
MTMKMMVHIYFVSLLLLLFHSYAIDIENEITEFFNKMRDTLPAKDSKWLNPACMFGGTMNDIAA
LGEPFSAKCPPIEDSLLSHRYKDYVVKWERLEKNRRRQVSNKRVKHGDLWIANYTSKFSNRRYL
CTVTTKNGDCVQGIVRSHIRKPPSCIPKTYELGTHDKYGIDLYCGILYAKHYNNITWYKDNKEI
NIDDIKYSQTGKELIIHNPELEDSGRYDCYVHYDDVRIKNDIVVSRCKILTVIPSQDHRFKLIL
DPKINVTIGEPANITCTAVSTSLLIDDVLIEWENPSGWLIGFDFDVYSVLTSRGGITEATLYFE
NVTEEYIGNTYKCRGHNYYFEKTLTTTVVLE

E3L mRNA sequence (SEQ ID NO:4)
5' GGGUAAUACAAGCUUGCUUGUUCUUUUUGCAGAAGCUCAGAAUAAACGCUCAACUUUGGCAG
AUCUGCCACCAUGUCUAAAAUCUAUAUCGACGAGCGUUCUAACGCAGAGAUUGUGUGUGAGGCU
AUUAAAACCAUUGGAAUCGAAGGAGCUACUGCUGCACAACUAACUAGACAACUUAAUAUGGAGA
AGCGAGAAGUUAAUAAAGCUCUGUACGAUCUUCAACGUAGUGCUAUGGUGUACAGCUCCGACGA
UAUUCCUCCUCGUUGGUUUAUGACAACGGAGGCGGAUAAGCCGGAUGCUGAUGCUAUGGCUGAC
GUCAUAAUAGAUGAUGUAUCCCGCGAAAAAUCAAUGAGAGAGGAUCAUAAGUCUUUUGAUGAUG
UUAUUCCGGCUAAAAAAAUUAUUGAUUGGAAAGGUGCUAACCCUGUCACCGUUAUUAAUGAGUA
CUGCCAAAUUACUAGGAGAGAUUGGUCUUUUCGUAUUGAAUCAGUGGGGCCUAGUAACUCUCCU
ACAUUUUAUGCCUGUGUAGACAUCGACGGAAGAGUAUUCGAUAAGGCAGAUGGAAAAUCUAAAC
GAGAUGCUAAAAAUAAUGCAGCUAAAUUGGCAGUAGAUAAACUUCUUGGUUACGUCAUCAUUAG
AUUCUGAACUAGUGACUGACUAGGAUCUGGUUACCACUAAACCAGCCUCAAGAACACCCGAAUG
GAGUCUCUAAGCUACAUAAUACCAACUUACACUUUACAAAAUGUUGUCCCCCAAAAUGUAGCCA
UUCGUAUCUGCUCCUAAUAAAAAGAAAGUUUCUUCACAUUCUGGAUCCUCUAGAGUCGA 3'

B.

E3L amino acid sequence (SEQ ID NO:5)
MSKIYIDERSNAEIVCEAIKTIGIEGATAAQLTRQLNMEKREVNKALYDLQRSAMVYSSDDIPP
RWFMTTEADKPDADAMADVIIDDVSREKSMREDHKSFDDVIPAKKIIDWKGANPVTVINEYCQI
TRRDWSFRIESVGPSNSPTFYACVDIDGRVFDKADGKSKRDAKNNAAKLAVDKLLGYVIIRF

K3L mRNA sequence (SEQ ID NO:6)
5' GGGUAAUACAAGCUUGCUUGUUCUUUUUGCAGAAGCUCAGAAUAAACGCUCAACUUUGGCAG
AUCUGCCACCAUGCUUGCAUUUUGUUAUUCGUUGCCCAAUGCGGGUGAUGUAAUAAAGGGCAGA
GUAUACGAGAAUGAUUAUGCUCUAUAUAUUUAUCUUUUUGACUAUCCUCACUUUGAAGCUAUCU
UGGCAGAGAGUGUUAAGAUGCAUAUGGAUAGAUAUGUUGAAUAUAGGGAUAAACUGGUAGGGAA
AACUGUAAAAGUUAAAGUGAUUAGAGUUGAUUAUACAAAAGGAUAUAUAGAUGUCAAUUACAAA
AGGAUGUGUAGACAUCAAUAAGAUAUCACUAGUGACUGACUAGGAUCUGGUUACCACUAAACCA
GCCUCAAGAACACCCGAAUGGAGUCUCUAAGCUACAUAAUACCAACUUACACUUUACAAAAUGU
UGUCCCCCAAAAUGUAGCCAUUCGUAUCUGCUCCUAAUAAAAAGAAAGUUUCUUCACAUUCUGG
AUCCUCUAGAGUCGA 3'

B.

K3L amino acid sequence (SEQ ID NO:7)
MLAFCYSLPNAGDVIKGRVYENDYALYIYLFDYPHFEAILAESVKMHMDRYVEYRDKLVGKTVK
VKVIRVDYTKGYIDVNYKRMCRHQ

SEQUENCE LISTING

```
<160> NUMBER OF SEQ ID NOS: 7

<210> SEQ ID NO 1
<211> LENGTH: 51
<212> TYPE: DNA
<213> ORGANISM: Artificial sequence
<220> FEATURE:
<223> OTHER INFORMATION: Synthetic

<400> SEQUENCE: 1
cagtttcact ttccccagtt tcactttccc cagtttcact ttccccagtt t          51

<210> SEQ ID NO 2
<211> LENGTH: 1368
<212> TYPE: RNA
<213> ORGANISM: Vaccinia virus

<400> SEQUENCE: 2
gggcgaauug gguaccgggc cccccucga ggucgacggu aucgauaagc uugcuuguuc    60
uuuuugcaga agcucagaau aaacgcucaa cuuuggcaga ucugauucga ggccaccaug   120
acgaugaaaa ugauggurca uauauauuuc guaucauuau uguuauugcu auccacagu    180 uacgccauag acaucgaaaa ugaaaucaca gaauucuuca auaaaaaugag agauacucua   240 ccagcuaaag acucuaaaug guugaaucca gcauguaugu ucggaggcac aaugaaugau   300
auagccgcuc uaggagagcc auucagcgca aaguguccuc cuauugaaga cagucuuuua   360
ucgcacagau auaaagacua uguggurcaaa ugggaaaggc uagaaaaaaaa uagacggcga   420
```

```
cagguuucua auaaacgugu uaaacauggu gauuuaugga uagccaacua acaucuaaa     480 uucaguaacc guagguauuu gugcaccgua acuacaaaga auggugacug uguucagggu    540
auaguuagau cucauauuag aaaccuccu ucaugcauuc caaaaacaua ugaacuaggu     600
acucaugaua aguauggcau agacuuauac ugugaauuc uuuacgcaaa acauuauaau     660
aauauaacuu gguauaaaga uaauaaggaa auuaauaucg acgacauuaa guauucacaa    720
acgggaaagg aauuaauuau ucauaauccu gaguuagaag auagcggaag auacgacugu    780
uacguucauu acgacgacgu uagaaucaag aaugauaucg uaguaucaag auguaaaaua    840
cuuacgguua uaccgucaca agaccacagg uuuaaacuaa uacuagaucc aaaaaucaac    900
guaacgauag gagaaccugc caauauaaca ugcacugcug ugucaacguc auuauugauu    960
gacgauguac ugauugaaug ggaaaauccaucc ggauggc uuauaggauu cgauuuugau  1020
guauacucug uuuuaacuag uagaggcggu auuaccgagg cgaccuugua cuuugaaaau   1080
guuacugaag aauauauagg uaauacauau aaaugucgug gacacaacua uuauuugaa    1140 aaaacccuua caacuacagu aguauuggag uaaaagcuau cacuagugac ugacuaggau    1200
cugguuacca cuaaaccagc cucaagaaca cccgaaugga gucucuaagc uacauaauac    1260
caacuuacac uuuacaaaau guugucccc aaaaugauag cauucguauc ugcuccuaau    1320
aaaaagaaag uuucuucaca uucuggaucc acuaguucua gagcggcc             1368
```

<210> SEQ ID NO 3
<211> LENGTH: 351
<212> TYPE: PRT
<213> ORGANISM: Vaccinia virus

<400> SEQUENCE: 3

```
Met Thr Met Lys Met Met Val His Ile Tyr Phe Val Ser Leu Leu Leu
1               5                   10                  15

Leu Leu Phe His Ser Tyr Ala Ile Asp Ile Glu Asn Glu Ile Thr Glu
            20                  25                  30

Phe Phe Asn Lys Met Arg Asp Thr Leu Pro Ala Lys Asp Ser Lys Trp
        35                  40                  45

Leu Asn Pro Ala Cys Met Phe Gly Gly Thr Met Asn Asp Ile Ala Ala
    50                  55                  60

Leu Gly Glu Pro Phe Ser Ala Lys Cys Pro Pro Ile Glu Asp Ser Leu
65                  70                  75                  80

Leu Ser His Arg Tyr Lys Asp Tyr Val Val Lys Trp Glu Arg Leu Glu
                85                  90                  95

Lys Asn Arg Arg Arg Gln Val Ser Asn Lys Arg Val Lys His Gly Asp
            100                 105                 110

Leu Trp Ile Ala Asn Tyr Thr Ser Lys Phe Ser Asn Arg Arg Tyr Leu
        115                 120                 125

Cys Thr Val Thr Thr Lys Asn Gly Asp Cys Val Gln Gly Ile Val Arg
    130                 135                 140

Ser His Ile Arg Lys Pro Pro Ser Cys Ile Pro Lys Thr Tyr Glu Leu
145                 150                 155                 160

Gly Thr His Asp Lys Tyr Gly Ile Asp Leu Tyr Cys Gly Ile Leu Tyr
                165                 170                 175

Ala Lys His Tyr Asn Asn Ile Thr Trp Tyr Lys Asp Asn Lys Glu Ile
            180                 185                 190

Asn Ile Asp Asp Ile Lys Tyr Ser Gln Thr Gly Lys Glu Leu Ile Ile
        195                 200                 205
```

-continued

```
His Asn Pro Glu Leu Glu Asp Ser Gly Arg Tyr Asp Cys Tyr Val His
    210                 215                 220

Tyr Asp Val Arg Ile Lys Asn Asp Ile Val Val Ser Arg Cys Lys
225                 230                 235                 240

Ile Leu Thr Val Ile Pro Ser Gln Asp His Arg Phe Lys Leu Ile Leu
                245                 250                 255

Asp Pro Lys Ile Asn Val Thr Ile Gly Glu Pro Ala Asn Ile Thr Cys
            260                 265                 270

Thr Ala Val Ser Thr Ser Leu Leu Ile Asp Asp Val Leu Ile Glu Trp
        275                 280                 285

Glu Asn Pro Ser Gly Trp Leu Ile Gly Phe Asp Phe Asp Val Tyr Ser
    290                 295                 300

Val Leu Thr Ser Arg Gly Gly Ile Thr Glu Ala Thr Leu Tyr Phe Glu
305                 310                 315                 320

Asn Val Thr Glu Glu Tyr Ile Gly Asn Thr Tyr Lys Cys Arg Gly His
                325                 330                 335

Asn Tyr Tyr Phe Glu Lys Thr Leu Thr Thr Thr Val Val Leu Glu
            340                 345                 350
```

<210> SEQ ID NO 4
<211> LENGTH: 825
<212> TYPE: RNA
<213> ORGANISM: Vaccinia virus

<400> SEQUENCE: 4

```
ggguaauaca agcuugcuug uucuuuuugc agaagcucag aauaaacgcu caacuuuggc      60
agaucugcca ccaugucuaa aaucuauauc gacgagcguu cuaacgcaga gauugugugu     120
gaggcuauua aaccauuugg aaucgaagga gcuacugcug cacaacuaac uagacaacuu     180
aauauggaga agcgagaagu aaauaaagcu cuguacgauc uucaacguag ugcuaugguug    240
uacagcuccg acgauauucc uccucguugg uuuaugacaa cggaggcgga uaagccggau     300
gcugaugcua uggcugacgu cauaauagau gauguauccc gcgaaaaauc aaugagagag     360
gaucauaagu cuuuugauga uguuauuccg gcuaaaaaaa uuauugauug gaaaggugcu     420
aacccuguca ccguuauuaa ugaguacugc caaauuacua ggagagauug gucuuuucgu     480
auugaaucag uggggccuag uaacucuccu acauuuuaug ccuguguaga caucgacgga     540
agauauuucg auaaggcaga uggaaaaucu aaacgagaug cuaaaauaa ugcagcuaaa     600
uuggcaguag auaaacuucu ugguuacguc aucauuagau ucugaacuag ugacugacua     660
ggaucugguu accacuaaac cagccucaag aacacccgaa uggagucucu aagcuacaua     720
auaccaacuu acacuuuaca aaauguuguc ccccaaaaug uagccauucg uaucugcucc     780
uaauaaaaag aaaguuucuu cacauucugg auccucuaga gucga                    825
```

<210> SEQ ID NO 5
<211> LENGTH: 190
<212> TYPE: PRT
<213> ORGANISM: Vaccinia virus

<400> SEQUENCE: 5

```
Met Ser Lys Ile Tyr Ile Asp Glu Arg Ser Asn Ala Glu Ile Val Cys
1               5                   10                  15

Glu Ala Ile Lys Thr Ile Gly Ile Glu Gly Ala Thr Ala Ala Gln Leu
                20                  25                  30

Thr Arg Gln Leu Asn Met Glu Lys Arg Glu Val Asn Lys Ala Leu Tyr
            35                  40                  45
```

```
Asp Leu Gln Arg Ser Ala Met Val Tyr Ser Ser Asp Asp Ile Pro Pro
    50                  55                  60

Arg Trp Phe Met Thr Thr Glu Ala Asp Lys Pro Asp Ala Asp Ala Met
65                  70                  75                  80

Ala Asp Val Ile Ile Asp Val Ser Arg Glu Lys Ser Met Arg Glu
                85                  90                  95

Asp His Lys Ser Phe Asp Val Ile Pro Ala Lys Lys Ile Ile Asp
            100                 105                 110

Trp Lys Gly Ala Asn Pro Val Thr Val Ile Asn Glu Tyr Cys Gln Ile
            115                 120                 125

Thr Arg Arg Asp Trp Ser Phe Arg Ile Glu Ser Val Gly Pro Ser Asn
    130                 135                 140

Ser Pro Thr Phe Tyr Ala Cys Val Asp Ile Asp Gly Arg Val Phe Asp
145                 150                 155                 160

Lys Ala Asp Gly Lys Ser Lys Arg Asp Ala Lys Asn Asn Ala Ala Lys
                165                 170                 175

Leu Ala Val Asp Lys Leu Leu Gly Tyr Val Ile Ile Arg Phe
                180                 185                 190

<210> SEQ ID NO 6
<211> LENGTH: 525
<212> TYPE: RNA
<213> ORGANISM: Vaccinia virus

<400> SEQUENCE: 6
ggguaauaca agcuugcuug uucuuuuugc agaagcucag aauaaacgcu caacuuuggc      60
agaucugcca ccaugcuugc auuuuguuau ucguugccca augcggguga uguaauaaag     120
ggcagaguau acgagaauga uuaugcucua uauauuuauc uuuuugacua uccucacuuu     180
gaagcuaucu uggcagagag uguuaagaug cauauggaua gauauguuga auauagggau     240
aaacugguag ggaaaacugu aaaaguuaaa gugauuagag uugauuauac aaaaggauau     300
auagauguca auuacaaaag gauguguaga caucaauaag auaucacuag ugacugacua     360
ggaucugguu accacuaaac cagccucaag aacacccgaa uggagucucu aagcuacaua     420
auaccaacuu acacuuuaca aaauguuguc ccccaaaaug uagccauucg uaucugcucc     480
uaauaaaaag aaaguuucuu cacauucugg auccucuaga gucga                    525

<210> SEQ ID NO 7
<211> LENGTH: 88
<212> TYPE: PRT
<213> ORGANISM: Vaccinia virus

<400> SEQUENCE: 7

Met Leu Ala Phe Cys Tyr Ser Leu Pro Asn Ala Gly Asp Val Ile Lys
1               5                   10                  15

Gly Arg Val Tyr Glu Asn Asp Tyr Ala Leu Tyr Ile Tyr Leu Phe Asp
                20                  25                  30

Tyr Pro His Phe Glu Ala Ile Leu Ala Glu Ser Val Lys Met His Met
            35                  40                  45

Asp Arg Tyr Val Glu Tyr Arg Asp Lys Leu Val Gly Lys Thr Val Lys
    50                  55                  60
```

```
Val Lys Val Ile Arg Val Asp Tyr Thr Lys Gly Tyr Ile Asp Val Asn
65                  70                  75                  80

Tyr Lys Arg Met Cys Arg His Gln
                85
```

INHIBITION OF INNATE IMMUNE RESPONSE

FIELD OF THE INVENTION

The present invention provides methods, kits, and compositions for reducing an innate immune system response in a human or animal cell, tissue or organism by introducing into the cell, tissue or organism an Agent mRNA comprising or consisting of mRNA encoding one or more proteins that affect the induction, activity and/or response of an innate immune response pathway; whereby, the innate immune response in the cell, tissue or organism is reduced compared to the innate immune response in the absence of introducing the Agent mRNA. Other embodiments are compositions or kits comprising an Agent mRNA for treating a disease or medical condition in a human or animal that exhibits symptoms of an elevated innate immune system, or for reducing an innate immune response that is induced in a human or animal cell, tissue or organism by a Foreign Substance that is administered to the cell, tissue or organism for a biological, medical, agricultural or research purpose.

BACKGROUND

The innate immune systems of humans and animals comprise a number of different mechanisms by which cells in these organisms recognize and respond to a variety of different pathogen-associated molecular patterns (PAMPS) on foreign substances or damage-associated (or danger-associated) molecular patterns due to components released due to damaged cells or stress signals from damaged cells (DAMPS). Pattern recognition receptor (PRR) proteins, including membrane-bound toll-like receptors (TLRs) and cytoplasmic NOD-like receptors (NLRs), recognize a variety of different ligands as foreign, damaged, or non-self (e.g., pathogen-associated or damage-associated) and activate one or more innate immune response pathways that function to defend the organism. In some cases, the innate immune response pathway may result in damage or death of the cell after binding of a ligand on a foreign substance to the PRR of the cell. For example, a type I interferon (IFN) response is induced upon binding of double-stranded RNA (dsRNA) to toll-like receptor 3 (TLR3) or binding of a Gram-negative lipopolysaccharide (LPS) to TLR4, and these IFN responses can inhibit protein translation in the cell and induce many other innate immune response pathways that result in damage to the cell, or, if sustained over time (e.g., by repeated exposure to the foreign substance comprising dsRNA or LPS over multiple days), result in death of the cell.

The Interferon family of cytokines is one key component of the innate immune response to both bacterial and viral infection. Interferons were discovered more than 50 years ago as biological agents that inhibited the replication of influenza virus (Isaacs and Lindenmann, 1957). Interferons are designated type I-III based on the receptor complex they signal through. Type I IFNs, which comprise 13 IFNα subtypes, IFNβ, IFNκ, IFNε, IFNo, IFNτ and IFNδ, engage the ubiquitously expressed IFNAR (IFNα receptor) complex that is composed of the IFNAR1 and IFNAR2 subunits. The functions of Type I IFNs are well characterized and known to be essential for mounting a robust anti-viral response (Muller et al., 1994). Type II IFNs consist of the single IFNγ protein that binds the IFNγ receptor (IFNGR) complex. IFNγ secretion functions primarily to inhibit pathogens other than viruses. Type III IFNs consist of 3 IFNλs and signal through IFNLR1 and IL-10R2. At present, not much is known regarding type III IFNs other than that they are known to regulate an antiviral response and may be the ancestral type I IFNs (Levraud et al., 2007).

Elevated type I IFN levels have been shown to play major roles in the disease states in autoimmune disorders such as psoriasis and systemic lupus erythematosus (SLE) (Hua et al., 2006; Kirou et al., 2005; Nestle et al., 2005). Neutralization of type I IFNs or type I IFN receptors with anti-interferon pathway-specific antibodies have been shown to reduce psoriasis and SLE disease progression (Nestle et al., 2005; Yao et al., 2009).

Viral infections initiate an innate immune response in infected cells resulting in a cascade of intracellular events, ultimately resulting in the secretion of interferons. Triggering the innate immune response can result in apoptosis of the cell or inhibition or repression of protein synthesis. Immunorecognition of viruses is dependent on detection of viral nucleic acids by PPRs, including TLRs. TLR3 activates an innate immune response by recognizing and binding to virally-derived dsRNA (Alexopoulou et al., 2001; Wang et al., 2004). TLR9 is activated by DNA containing unmethylated CpG motifs, found in viral and bacterial DNA (Hemmi et al., 2000). Single-stranded RNAs (ssRNA) and small interfering RNA (siRNAs) are recognized by TLR7 and TLR8 (Diebold et al., 2004; Heil et al., 2004; Hemmi et al., 2002; Judge and MacLachlan, 2008). TLR4 activates an innate immune response by recognizing and binding to LPS of Gram-negative bacteria. Innate immune responses induced by different foreign substances activating different TLRs can be mediated, at least in part, through common signaling pathways. For example, activation of both TLR3 and TLR4 trigger signaling pathways that result in production of type I interferons (IFNs).

Vaccinia virus (VV), a cytoplasmic DNA virus in the poxvirus family, encodes a set of intracellular proteins or soluble cytokine binding proteins that enhance virus virulence. VV intracellular E3L protein, an inhibitor of interferon induction, binds to dsRNA and prevents the activation of the IFN-induced protein kinase PKR (Chang et al., 1992). VV intracellular K3L protein binds competitively to PKR and blocks the phosphorylation and inactivation of host eIF-2α (Beattie et al., 1991). VV also encodes a secreted IFNα/β receptor that is encoded by the B18R gene (Colamonici et al., 1995; Symons et al., 1995). This B18R gene encodes a secreted glycoprotein that binds to and inhibits the function of type I interferons (IFNα/β), while not binding nor inhibiting type II interferons (IFNγ) (Symons et al., 1995). Vaccinia strains lacking functional B18R show much lower levels of viral virulence demonstrating the importance of inhibiting type I interferons during viral infection (Colamonici et al., 1995; Symons et al., 1995).

In vitro-transcribed mRNA made from SP6, T7 or T3 RNA polymerases have been shown to function in countless studies when used for direct injection into *Xenopus laevis* (frog) or *Danio rerio* (zebrafish) ooyctes as well as for transfection into mammalian cells in culture. It is well established that in vitro transcription using T7 RNA polymerase can result in the generation of some dsRNA in addition to the desired ssRNA (Cazenave and Uhlenbeck, 1994; Triana-Alonso et al., 1995). Introduction of viral dsRNA or the synthetic dsRNA cohomopolymer polyinosinic-polycytidylic acid (polyI:C) results in the activation of a TLR3-mediated innate immune response (Alexopoulou et al., 2001; Schulz et al., 2005). Similarly, introduction of in vitro-transcribed mRNA or dsRNA into mammalian cells results in the activation of TLR3-mediated innate immune response, signified by the production of type I interferons (Kariko et al., 2004). Addition of recombinant B18R protein to the media of cells transfected with in vitro-transcribed mRNAs reduces mRNA-induced toxicity, presumably through the inhibition of interferon activity (Angel and Yanik, 2010; Warren et al., 2010); and U.S. Patent Application No. 20100273220)

SUMMARY OF THE INVENTION

The present invention comprises methods, kits, systems, and compositions for reducing, suppressing or preventing an innate immune system response that is induced in a human or animal cell, tissue or organism. One embodiment is a method for reducing, suppressing and/or preventing an innate immune response in a human or animal cell, tissue or organism, comprising: introducing into the cell, tissue or organism an Agent mRNA comprising or consisting of mRNA (e.g., in vitro synthesized mRNA) encoding one or more proteins that affect the induction, activity or response of an innate immune response pathway; whereby, the innate immune response in the cell, tissue or organism is reduced, suppressed or prevented compared to the innate immune response in the absence of introducing the Agent mRNA. Other embodiments are compositions or kits comprising an Agent mRNA.

In some embodiments of the methods, compositions and kits, the Agent mRNA comprises or consists of one or more mRNAs encoding one or more proteins that reduces the activity an innate immune response. In some embodiments, Agent mRNA encodes a protein that binds a biochemical molecule (e.g., a protein) in a cell that mediates said innate immune response, which binding reduces the innate immune response. In some embodiments, Agent mRNA encodes an antibody or artificial antibody that binds a biochemical molecule (e.g., a protein) that mediates said innate immune response in a cell, which binding reduces the innate immune response.

In some embodiments of the methods, compositions and kits, the Agent mRNA comprises or consists of one or more mRNAs encoding one or more proteins that inhibits the activity of an innate immune effector protein in a signaling pathway mediated by a TLR selected from the group consisting of TLR1, TLR2, TLR3, TLR4, TLR5, TLR6, TLR7, TLR8, TLR9 and TLR10. In some embodiments, the Agent mRNA encodes a biologically active fragment, analog or variant of any of said proteins.

In some embodiments of the methods, compositions and kits, the Agent mRNA comprises or consists of one or more mRNAs encoding a biologically inactive fragment, mutant, analog or variant or a dominant negative functional inhibitor of one or more proteins selected from the group consisting of: TP53, TLR3, TLR4, TLR7, TLR8, RARRES3, IFNA1, IFNA2, IFNA4, IFNA5, IFNA6, IFNA7, IFNA8, IFNA10, IFNA13, IFNA14, IFNA16, IFNA17, IFNA21, IFNK, IFNB1, IL6, TICAM1, TICAM2, MAVS, STAT1, STAT2, EIF2AK2, IRF3, TBK1, CDKN1A, CDKN2A, RNASEL, IFNAR1, IFNAR2, OAS1, OAS2, OAS3, OASL, RB1, ISG15, MX1, IRF9, ISG20, IFIT1, IFIT2, IFIT3, IFIT5, PKR, RIG-1, MDA5, NF-κB, TRIF, Tyk2, and IRF7.

As used herein, a "biologically inactive fragment, mutant, analog or variant of a protein" or a "dominant negative inhibitor" means a fragment, mutant, analog or variant of a wild-type protein that interacts with the same cellular molecules as the biologically active wild-type protein, but which, due to a lack of certain amino acids or moieties in said biologically inactive, fragment, mutant, analog or variant (of a) protein compared to said wild-type protein, said interaction with said biologically inactive, fragment, mutant, analog or variant protein is not biologically active and blocks some aspect of the normal biological function compared to the interaction with the wild-type protein.

In some embodiments of the methods, compositions and kits, the Agent mRNA comprises or consists of mRNA encoding one or more protein inhibitors (e.g., one or more antibodies or artificial antibodies) that inhibit the functions of one or more proteins selected from the group consisting of: TP53, TLR3, TLR4, TLR7, TLR8, RARRES3, IFNA1, IFNA2, IFNA4, IFNA5, IFNA6, IFNA7, IFNA8, IFNA10, IFNA13, IFNA14, IFNA16, IFNA17, IFNA21, IFNK, IFNB1, IL6, TICAM1, TICAM2, MAVS, STAT1, STAT2, EIF2AK2, IRF3, TBK1, CDKN1A, CDKN2A, RNASEL, IFNAR1, IFNAR2, OAS1, OAS2, OAS3, OASL, RB1, ISG15, MX1, IRF9, ISG20, IFIT1, IFIT2, IFIT3, IFIT5, PKR, RIG-1, MDA5, NF-κB, TRIF, Tyk2, and IRF7.

In some embodiments of the methods, compositions and kits, the Agent mRNA comprises or consists of one or more mRNAs encoding one or more proteins that is a regulator or inhibitor of type I-interferon signaling, induction, or response.

In some embodiments, Agent mRNA encodes an antibody or artificial antibody that binds a biochemical molecule (e.g., a protein) that mediates a type I-mediated innate immune response in a cell, which binding reduces the type I-mediated innate immune response.

In some embodiments of the methods, compositions and kits, the Agent mRNA comprises or consists of mRNA encoding one or more protein inhibitors (e.g., one or more antibodies or artificial antibodies) that inhibits type I-interferon signaling, induction, or response.

In some embodiments of the methods, compositions and kits, the Agent mRNA comprises or consists of one or more mRNAs encoding one or more proteins selected from the group consisting of: Vaccinia virus B18R protein, Vaccinia virus E3L protein, Vaccinia virus K3L protein, Influenza A virus NS1 protein, human papilloma virus 18 protein E6, human interferon alpha/beta binding proteins, soluble forms of the human interferon alpha receptors, INFAR1, 1INFAR2, or a biologically active fragment, analog or variant of any of said proteins.

In some embodiments, the methods, compositions or kits are used to treat a disease or medical condition in a human or animal that exhibits an elevated innate immune system response. In some embodiments, the methods, compositions or kits are used to treat a disease or medical condition in a human or animal that exhibits an elevated innate immune system response comprising or consisting of an elevated type I IFN-mediated innate immune response (e.g., as exhibited by an elevated level of type I IFN production or response). In some of these embodiments of methods, kits, systems or compositions, the Agent mRNA encodes one or more proteins that reduce or suppress an innate immune response comprising an elevated level of type I IFN production or response. For example, in certain embodiments, the Agent mRNA encoding one or more proteins that reduce or suppress an innate immune response comprising an elevated level of type I IFN production or response is selected from the group consisting of B18R protein, E3L protein, K3L protein or a biologically active fragment, analog or variant of any of said proteins.

In some embodiments, the Agent mRNA encoding innate immune inhibitors results in reduction of elevated type I interferon production in diseases like psoriasis or systemic lupus erythematosus (SLE). In further embodiments, the Agent mRNA (e.g., encoding one or more proteins that reduces or suppresses type I IFN production or response, such as B18R protein, E3L protein, and K3L protein is administered systemically (with or without complexing of Agent mRNA to a transfection reagent) e.g., by vascular injection; in a liquid or cream delivered topically to the skin; as an aerosol delivered into the lungs; or by electroporation or injection directly into a tissue, such as heart, liver, muscle, brain, pancreas tissue or any other organ or tissue to reduce elevated type I IFN production in diseases like psoriasis, SLE or other diseases caused by upregulation of type I interferon production, including diseases for which the cause has not yet been identified and characterized. In certain preferred embodiments, the methods, kits and compositions results in reduction of elevated type I interferon production for treatment of psoriasis or SLE.

In other embodiments, the methods, composition and kits find utility for reducing, suppressing or preventing an innate immune response that is induced in a human or animal cell, tissue or organism by a Foreign Substance that is administered to the cell, tissue or organism for a biological, medical, agricultural or research purpose. Thus, in some embodiments of the methods, said innate immune response that is reduced, suppressed or prevented is caused by introduction of a Foreign Substance that is capable of causing an innate immune response in said cell, tissue or organism by affecting the induction, activity or response of an innate immune response pathway in said cell, tissue or organism.

As used herein, a "Foreign Substance" means any molecule or ligand against which a cell, tissue or organism responds by initiating an innate immune response involving one or more innate immune response pathways. For example and without limitation, said molecule or ligand can be recognized through binding to a PRR, such as a TLR or NLR, as being foreign, non-self, a PAMP or a DAMP. Furthermore, for example, but without limitation, certain Gram-negative bacterial lipopolysaccharides are Foreign Substances because, once they are recognized by binding to TLR4 on a cell, an innate immune response comprising a type I interferon response is induced. Similarly, certain dsRNA (e.g., double stranded RNA longer than about 25 bases) is a Foreign Substance because it binds to TLR3 on a cell, which in turn results in induction of an innate immune response comprising a type I interferon response.

One embodiment of the invention is a method for reducing, suppressing or preventing an innate immune response in a human or animal cell, tissue or organism generated by a Foreign Substance, comprising: introducing to the cell, tissue or organism an effective amount of Agent mRNA encoding one or more proteins that affect the induction, activity or response of an innate immune response pathway; whereby, the innate immune response in the cell, tissue or organism is reduced, suppressed or prevented compared to the innate immune response in the absence of introducing the Agent mRNA. In certain embodiments of the method, the Foreign Substance is Exogenous RNA.

In certain embodiments, the Exogenous RNA is Exogenous mRNA. In certain embodiments, introduction of Agent mRNA results in an increase in translation of the Exogenous mRNA in the human or animal cell and/or a decrease in toxicity (resulting in increased cell survival) of the Exogenous mRNA to the cell, tissue or organism compared to the toxicity (or cell survival) in the absence of the Agent mRNA.

In certain embodiments, the Foreign Substance is Exogenous siRNA or Exogenous miRNA. In certain embodiments, introduction of Agent mRNA results in an increase in the specificity (e.g., a decrease in the off-target Exogenous siRNA- or Exogenous miRNA-mediated decrease in expression compared to the same results in the absence of the Agent mRNA). In certain embodiments, introduction of Agent mRNA results in a decrease in toxicity (or increase in cell survival) or a decrease in translational inhibition induced by introducing Exogenous siRNA or Exogenous miRNA to the cell, tissue or organism compared to the toxicity (or cell survival) or translational inhibition in the absence of the Agent mRNA.

In certain embodiments, the method results in a biological effect in the cells, tissue or organism. In certain embodiments, the Agent mRNA encodes one or more proteins that reduce the innate immune response induced by contacting the cell with a Foreign Substance (e.g., an LPS, (e.g., comprising or consisting of a Gram-negative bacterial LPS), a double stranded RNA (dsRNA), or Exogenous RNA).

In certain embodiments, the Agent mRNA encodes one or more proteins that reduces the innate immune response outside of the cell (i.e., extracellularly); e.g., wherein the protein encoded by the Agent mRNA is a secreted protein, such as B18R protein.

In certain embodiments, the Agent mRNA encodes one or more proteins that reduce the innate immune response inside of the cell (i.e., intracellularly); e.g., wherein the protein encoded by the mRNA remains within the cell, such as E3L or K3L proteins. Those with knowledge in the field will understand that it is very difficult to reliably deliver an intracellular protein into a cell efficiently and in active form. The present method of reducing, suppressing or preventing an innate immune response by introducing to the cells, tissues or organism, an Agent mRNA encoding such intracellular proteins provides important advantages and benefits over all methods previously known in the art. In certain embodiments, the Agent mRNA encodes a protein that reduces or suppresses the type I interferon-induced cellular toxicity or translation inhibition resulting from the cellular transfection or introduction of a Foreign Substance comprising or consisting of Exogenous mRNA. In certain embodiments, the Agent mRNA encodes a protein that reduces the type I interferon-induced cellular toxicity or translation inhibition resulting from contacting the cell with another Foreign Substance (e.g., a Gram-negative bacterial LPS or a viral dsRNA).

One embodiment of the invention is a method for reducing, suppressing or preventing an innate immune response in a human or animal cell, tissue or organism generated by a Foreign Substance, comprising: introducing to the cell, tissue or organism an effective amount of Agent mRNA encoding one or more proteins that affect the induction, activity or response of an innate immune response pathway; whereby, the innate immune response in the cell, tissue or organism is reduced, suppressed or prevented compared to the innate immune response in the absence of introducing the Agent mRNA. In certain embodiments, the present invention is a method for reducing, suppressing or preventing the innate immune response of a human or animal cell, tissue or organism caused by transfection of the cell with Exogenous RNA (e.g. Exogenous mRNA) or with Exogenous siRNA or Exogenous miRNA, comprising: introducing to the cell (e.g., a cell culture medium or in a in a tissue or organism) an effective amount of an Agent mRNA encoding one or more proteins that affect the induction, activity or response of an innate immune response pathway; whereby, the innate immune response in the cell is reduced, suppressed or prevented compared to the innate immune response in the absence of introducing the Agent mRNA (i.e., the innate immune response following transfection of the cell with the Exogenous RNA (e.g. Exogenous mRNA) or with Exogenous siRNA or Exogenous miRNA is reduced, suppressed or prevented compared to the innate immune response following transfection of the cell with the Exogenous RNA (e.g. Exogenous mRNA) or with Exogenous siRNA or Exogenous miRNA without the introduction of the Agent mRNA). In certain embodiments, the Exogenous RNA comprises or consists of Exogenous mRNA that results in a biological effect in the cell. In some preferred embodiments, said introducing into the cell of the Agent mRNA results in a higher rate of cell survival (i.e., a lower rate of cell death) (e.g., a 25% . . . 50% . . . 100% . . . or >100% higher rate of cell survival) following transfection of the cell with the Exogenous RNA compared to the rate of cell survival in the absence of introducing to the cell of the Agent mRNA. In some preferred embodiments, the Exogenous RNA is Exogenous mRNA and said introducing into the cell of the Agent mRNA results in a higher translation of said Exogenous mRNA into protein following said transfection of the cell compared to the level of translation in the absence of introducing to the cell of the Agent mRNA (e.g., a 10% . . . 25% . . . 50% . . . 75% . . . 100% . . . or >100% higher level of translation in a cell compared to the level of translation in a cell transfected with the same amount of Exogenous mRNA but without the Agent mRNA).

In certain embodiments of any of the methods comprising transfection of a Foreign Substance comprising Exogenous siRNA or Exogenous miRNA into the cell, tissue or organism, the Foreign Substance comprising Exogenous siRNA or Exogenous miRNA results in a biological effect in the cell, tissue or organism. In some preferred embodiments, introducing of Agent mRNA into the cell, tissue or organism into which the Foreign Substance comprising Exogenous siRNA or Exogenous miRNA is transfected results in a higher level of specificity or a lower level of off-target effects. In certain embodiments, introduction of Agent mRNA results in a decrease in toxicity (or increase in cell survival) or a decrease in translational inhibition induced by said transfection of the Foreign Substance comprising Exogenous siRNA or Exogenous miRNA to the cell, tissue or organism compared to the toxicity (or cell survival) or translational inhibition in the absence of the Agent mRNA. In some preferred embodiments, said transfection of said Exogenous RNA (e.g., Exogenous mRNA) or said Exogenous siRNA or Exogenous miRNA comprises or consists of multiple sequential transfections of said cell, tissue or organism with said Exogenous RNA (e.g., Exogenous mRNA) or said Exogenous siRNA or Exogenous miRNA (e.g., multiple transfections at daily, 2-day, 3-day, 4-day, 5-day, 6-day, weekly, or monthly intervals or any other intervals or combination of intervals that is found to be effective for a particular purpose). In some preferred embodiments, said introducing into the cell of the Agent mRNA is made together with or at approximately the same time as said transfection of the cell with said Exogenous RNA. In some embodiments, said introducing into the cell of the Agent mRNA is made prior to said transfection of the cell with said Exogenous RNA. In certain embodiments, in addition to introducing said Agent mRNA, the method further comprises introducing to the cell the protein encoded by said Agent mRNA.

In some preferred embodiments, said translation of said Exogenous mRNA into protein following said transfection of the cell results in a biological effect. In some preferred embodiments, said biological effect comprises or consists of: reprogramming of said cell. In some embodiments, said reprogramming comprises or consists of: (i) induction of a differentiated cell into a pluripotent stem cell (or "induced pluripotent stem cell" or "iPS cell" or "iPSC"); (ii) differentiation of an embryonic stem cell ("eSC") or iPSC into a cell that exhibits a more highly specialized state of differentiation; or (iii) transdifferentiation of a cell from one state of differentiation to a second state of differentiation.

In some other preferred embodiments, said biological effect comprises or consists of: translation of a protein that is defective or lacking in a cell of a human or animal patient that has an error of metabolism (e.g., due to an inherited genetic disease or a de novo mutation that results in a missing or defective gene product, including a missing or defective gene product comprising or consisting of mRNA and/or protein). Thus, in some embodiments of the methods, kits and compositions, the Foreign Substance is Exogenous RNA (e.g., Exogenous mRNA) and said Exogenous mRNA encodes the protein that is defective or lacking in said cell, tissue or organism (e.g., due to the inherited genetic disease or a de novo mutation that results in a missing or defective gene product).

In some other preferred embodiments of the method, said cell into which the Exogenous mRNA is transfected is an antigen-presenting cell or "APC" (e.g., a dendritic cell, a macrophage, a Langerhans cell, a Kuppfer cell and an artificial APC) and said Exogenous mRNA that is transfected comprises or consists of one or multiple mRNAs derived from a cancer cell from a human or animal patient (e.g., wherein said mRNAs are made by in vitro transcription (IVT) of cDNA generated from substantially all of the mRNA isolated from one or more cancer cells; e.g., wherein the IVT is part of a method comprising amplification of sense RNA; e.g. as described in U.S. Pat. No. 8,039,214); in some preferred embodiments of this method, the cell that is transfected with the Exogenous mRNA is used for immunotherapy of a patient that exhibits the cancer; in some embodiments, the Exogenous mRNA that is used for transfection of the APC is derived or prepared from a cancer cell from the patient and the APC that is transfected is derived or prepared from the same patient with the cancer; whereas in some other embodiments, the Exogenous mRNA that is used for transfection of the APC is derived or prepared from a cancer cell from a different patient or is genetically engineered or chemically synthesized based on knowledge of one or more known gene products that are expressed in a cancer cell of the type from which the patient suffers (e.g., preferably, wherein the one or more gene products expressed in the cancer cell are not expressed or are expressed at a much lower level in a cell of the same type but without the cancer); and in some embodiments the APC is derived or prepared from another human or animal, including from a cultured human or animal cell, including from an ex vivo-differentiated cell. In some preferred embodiments of the method, said transfection of said cell (e.g., an APC) with said Exogenous RNA (e.g., Exogenous mRNA) comprises or consists of transfection of said cell in vivo in a human or animal (e.g., following intradermal, subdermal, or internodal injection).

In further embodiments of any of the methods comprising introducing into the cell an effective amount of an Agent mRNA encoding a protein that reduces or suppresses an innate immune response, prior to introducing to the cell said Agent mRNA, the method further comprises the step of: contacting the cell with a protein that effectively reduces the innate immune response due to the Agent mRNA itself; this embodiment prevents or reduces the innate immune response from said introducing of said Agent mRNA encoding a protein that reduces or suppresses an innate immune response until such time as said Agent mRNA is active (e.g., until such time as said Agent mRNA that encodes said protein is expressed in said cell). In certain embodiments of the method, wherein the Agent mRNA encodes a protein that reduces or suppresses an innate immune response by extracellular binding (e.g., Agent mRNA encoding Vaccinia virus B18R protein or a biologically active fragment, analog or variant thereof), the method further comprises contacting the cell with the protein encoded by said Agent mRNA that encodes the extracellular protein prior to said introducing into the cell the Agent mRNA. In some preferred embodiments, the agent mRNA encodes the Vaccinia virus B18R protein or a biologically active fragment, analog or variant thereof and the protein that effectively reduces the innate immune response due to the Agent mRNA is the Vaccinia virus B18R protein or a biologically active fragment, analog or variant thereof. In other embodiments, said protein that effectively reduces the innate immune response due to the Agent mRNA is one or more other proteins that reduces a type 1 interferon response in said cell.

In additional embodiments, the present invention is a kit or system comprising or consisting of: a) an Agent mRNA that reduces or suppresses the innate immune response in a cell that is induced by a Foreign Substance (e.g., a Foreign Substance comprising or consisting of a LPS, dsRNA, Exogenous RNA, or Exogenous siRNA or Exogenous miRNA), and b) an Exogenous RNA (e.g., an Exogenous mRNA) or Exogenous siRNA or Exogenous miRNA. In certain embodiments, the Agent mRNA encodes a protein that reduces or suppresses the innate immune response induced in the cell by the Foreign Substance (e.g., induced by transfection with the Exogenous RNA or Exogenous siRNA or Exogenous miRNA). In certain embodiments, the kit or system further comprises the protein encoded by the Agent mRNA. In certain embodiments of a composition or a kit comprising an Agent mRNA encoding a protein that reduces and/or suppresses an innate immune response by intracellular binding or action (e.g., E3L or K3L mRNA), the composition or kit further comprises a protein that reduces or suppresses an innate immune response by extracellular binding or after being secreted from the cell (e.g., B18R protein). In certain embodiments of a composition or a kit comprising an Agent mRNA encoding a protein that reduces or suppresses an innate immune response by extracellular binding or after being secreted from the cell (e.g., Agent mRNA encoding B18R protein), the composition or kit further comprises a protein that reduces or suppresses an innate immune response encoded by said Agent mRNA or another protein that reduces or suppresses an innate immune response by extracellular binding or after being secreted from the cell. In certain embodiments, the kit further comprises the cell.

In some embodiments, the present invention provides a composition comprising or consisting of an Agent mRNA that reduces an innate immune response after being introduced into a cell, tissue or organism. In some embodiments, the present invention provides a composition comprising or consisting of: a) an Agent mRNA that reduces the innate immune response in a cell, tissue or organism that is induced by transfection with Exogenous RNA (e.g., Exogenous mRNA) or Exogenous siRNA or Exogenous miRNA, and b) the Exogenous RNA or Exogenous siRNA or Exogenous miRNA. In certain embodiments, the composition further comprises the cell.

In particular embodiments of methods, kits or compositions, the Agent mRNA encodes a protein that reduces the biological activity of a protein in an innate immune response pathway. In some embodiments, the protein encoded by said Agent mRNA is a viral-encoded protein. In some embodiments of methods, kits or compositions, the Agent mRNA further comprises a small molecule that reduces the biological activity of a protein in an innate immune response pathway. In further embodiments, the methods, compositions, or kits use or comprise an Agent mRNA that comprises or consists of two or more different RNAs (e.g., two or more mRNAs encoding two or more different proteins). In some embodiments, the proteins that effectively reduce or suppress the innate immune encoded by Agent mRNA comprise one or more other proteins that reduces a type 1 interferon response in the cell, tissue or organism. In some preferred embodiments, the Agent mRNA encodes the Vaccinia virus B18R protein or a biologically active fragment, analog or variant thereof, and the protein effectively reduces the innate immune response due to the Agent mRNA is the Vaccinia virus B18R protein or a biologically active fragment, analog or variant thereof.

In certain embodiments of any of the methods, kits systems or compositions, the Agent mRNA encodes one, two or more proteins selected from the group consisting of B18R protein, E3L protein, K3L protein, or a biologically active fragment, analog or variant of any thereof. In other embodiments, the methods, kits, systems and compositions herein employ two or more of B18R protein, E3L protein, K3L protein (or biologically active fragments thereof).

In certain embodiments, the Agent mRNA encodes a protein inhibitor of type I-interferon signaling, induction, or response. In further embodiments, the Agent mRNA molecule that encodes a protein inhibitor is selected from the group consisting of: Vaccinia virus B18R protein, human interferon alpha/beta binding proteins, soluble forms of the human interferon alpha receptors (e.g., IFNARs; see, U.S. Pat. No. 6,458,932; European Patent No. EP0679717 B1), including INFAR1 and 1INFAR2, or a biologically active fragment, analog or variant of any thereof. In further embodiments, the Agent mRNA encodes Vaccinia virus B18R protein, Vaccinia virus E3L protein (an inhibitor of interferon induction), Vaccinia virus K3L protein (an inhibitor of PKR, which is an effector protein activated by interferon signaling), Influenza A virus NS1 protein (an inhibitor of interferon induction), Human papilloma virus 18 protein E6 (an interferon signaling inhibitor), human interferon alpha/beta binding proteins, soluble forms of the human interferon alpha receptors, including INFAR1 and 1INFAR2, or a biologically active fragment, analog or variant of any thereof. In additional embodiments, the Agent mRNA comprises or consists of one or more mRNAs that encodes a biologically inactive fragment, mutant, analog or variant or a dominant negative functional inhibitor of one or more positive effector proteins in an innate immune response pathway, wherein said biologically inactive fragment, mutant, analog or variant is of a protein selected from the group consisting of: TP53, TLR3, TLR4, TLR7, TLR8, RARRES3, IFNA1, IFNA2, IFNA4, IFNA5, IFNA6, IFNA7, IFNA8, IFNA10, IFNA13, IFNA14, IFNA16, IFNA17, IFNA21, IFNK, IFNB1, IL6, TICAM1, TICAM2, MAVS, STAT1, STAT2, EIF2AK2, IRF3, TBK1, CDKN1A, CDKN2A, RNASEL, IFNAR1, IFNAR2, OAS1, OAS2, OAS3, OASL, RB1, ISG15, MX1, IRF9, ISG20, IFIT1, IFIT2, IFIT3, IFIT5, PKR, RIG-1, MDA5, NF-κB, TRIF, Tyk2 and IRF7. In additional embodiments of the methods, compositions and kits, the Agent mRNA comprises or consists of one or more mRNAs that encodes a protein that is a receptor in an innate immune response signaling pathway mediated by a TLR. In some embodiments of the methods, compositions and kits, in addition to the Agent mRNA, the composition or kit or system further comprises a biologically inactive fragment, mutant, analog or variant or a dominant negative functional inhibitor of one or more positive effector proteins selected from the group consisting of: TP53, TLR3, TLR4, TLR7, TLR8, RARRES3, IFNA1, IFNA2, IFNA4, IFNA5, IFNA6, IFNA7, IFNA8, IFNA10, IFNA13, IFNA14, IFNA16, IFNA17, IFNA21, IFNK, IFNB1, IL6, TICAM1, TICAM2, MAVS, STAT1, STAT2, EIF2AK2, IRF3, TBK1, CDKN1A, CDKN2A, RNASEL, IFNAR1, IFNAR2, OAS1, OAS2, OAS3, OASL, RB1, ISG15, MX1, IRF9, ISG20, IFIT1, IFIT2, IFIT3, IFIT5, PKR, RIG-1, MDA5, NF-κB, TRIF, Tyk2 and IRF7. In still other embodiments, the methods, compositions systems, and kits, further comprises a biologically inactive fragment, mutant, analog or variant or a dominant negative functional inhibitor of one or more positive effector proteins selected from the group consisting of: TP53, TLR3, TLR4, TLR7, TLR8, RARRES3, IFNA1, IFNA2, IFNA4, IFNA5, IFNA6, IFNA7, IFNA8, IFNA10, IFNA13, IFNA14, IFNA16, IFNA17, IFNA21, IFNK, IFNB1, IL6, TICAM1, TICAM2, MAVS, STAT1, STAT2, EIF2AK2, IRF3, TBK1, CDKN1A, CDKN2A, RNASEL, IFNAR1, IFNAR2, OAS1, OAS2, OAS3, OASL, RB1, ISG15, MX1, IRF9, ISG20, IFIT1, IFIT2, IFIT3, IFIT5, PKR, RIG-1, MDA5, NF-κB, TRIF, Tyk2 and IRF7. In additional embodiments of the methods, compositions and kits, the Agent mRNA encodes a protein that is a biologically active soluble receptor in an innate immune response signaling pathway, or a biologically active fragment, analog or variant thereof. In additional embodiments of the methods, compositions and kits, the Agent mRNA encodes a protein that is an inhibitor that binds a protein in a signaling pathway mediated by a TLR selected from the group consisting of TLR1, TLR2, TLR3, TLR4, TLR5, TLR6, TLR7, TLR8, TLR9 and TLR10. In some embodiments of the methods, compositions and kits, the Agent mRNA encodes a an antibody or artificial antibody that reduces an innate immune response by binding a protein in a signaling pathway mediated by a TLR selected from the group consisting of TLR1, TLR2, TLR3, TLR4, TLR5, TLR6, TLR7, TLR8, TLR9 and TLR10.

In additional embodiments of the methods, compositions, systems, and kits, the Agent mRNA encodes one or more function-blocking antibodies that reduces or suppresses the activity of a protein in an innate immune response pathway. In some embodiments, the sequence of an mRNA encoding an antibody that reduces an innate immune response is first made in a non-human species and then, using any of the methods known in the art, the Agent mRNA in made by modifying the sequence so that the protein encoded by said Agent mRNA is similar to an antibody which would be produced naturally in humans; the antibody encoded by said Agent mRNA is then said to be "humanized" because it is has been adapted to be suitable for use in humans with minimal chance of inducing an active immune response. Agent mRNA encoding antibodies intended for use in other species can be similarly adapted for use in those species.

In some embodiments of the methods, kits, systems, and compositions, the cell is a human or animal cell comprising said cell, tissue or organism, selected from the group consisting of: a fibroblast cell, such as fetal and neonatal fibroblasts or adult fibroblasts, an hematopoietic cell, a B cell, a T cell, an APC, including a dendritic cell, a macrophage cell, a Langerhans cell, or an artificial APC, a Kuppfer cell, a monocyte, mononuclear cells, a keratinocyte cell, in particular a primary keratinocyte, more preferably a keratinocyte derived from hair, an adipose cell, an epithelial cell, an epidermal cell, a chondrocyte, a cumulus cell, a neural cell, a glial cell, an astrocyte, a cardiac cell, an esophageal cell, a muscle cell, a melanocyte, and an osteocyte.

In additional embodiments of the methods, kits and compositions, the Exogenous mRNA encodes a secreted protein, a cell surface receptor, intracellular signaling mediator or a transcription factor. In particular embodiments, the Exogenous mRNA encodes a protein in the family selected from the group consisting of OCT3/4, SOX2, KLF4, c-MYC, c-MYC(T58A), L-MYC, NANOG, LIN28, SV40 Large-T antigen, hTERT, E-Cadherin, and MYOD1, SHH, GLI1, RARγ, LRH1, GLIS1, NURR1, MASH1, LMX1A, BRN2, MYT1L, GATA4, MEF2C, TBX5, HAND2, FOXA1, FOXA2, FOXA3, HNF1α, HNF4α, PAX3, and PAX7. In further embodiments, the introducing to the cell of an effective amount of an Agent mRNA encoding a protein that reduces or suppresses an innate immune response enhances mRNA-mediated iPS cell generation from somatic cells by repeated transfections with Exogenous mRNA encoding one or more proteins selected from the group consisting of KLF4, LIN28, c-MYC, L-MYC, c-MYC(T58A), OCT3/4, SOX2, NANOG, GLIS1, RARγ, LRH1, and E-CADHERIN.

In other embodiments, the introducing to the cell of an effective amount of an Agent mRNA encoding a protein that reduces or suppresses the innate immune response enhances transdifferentiation of one cell type into a second cell type. In further embodiments, the introducing to the cell of an effective amount of an Agent mRNA encoding a protein that reduces the innate immune response enhances differentiation of iPSCs, embryonic stem cells, or lineage-restricted stem cells (e.g., mesenchymal, hematopoietic, or neuronal stem cells) with Exogenous mRNA encoding factors known to direct stem cells toward various specific downstream lineages or cell types.

In some embodiments of the methods, kits and compositions, the Foreign Substance is Exogenous mRNA encoding one or more proteins selected from the group consisting of a secreted protein, a cell surface receptor, an intracellular signaling mediator, and a transcription factor, particularly wherein, said transcription factor is a transcription factor protein in the family selected from the group consisting of: OCT3/4, SOX2, KLF4, c-MYC, c-MYC(T58A), L-MYC, NANOG, LIN28, SV40 Large-T antigen, hTERT, E-Cadherin, MYOD1, SHH, GLI1, RARγ, LRH1, GLIS1, NURR1, MASH1, LMX1A, BRN2, MYT1L, GATA4, MEF2C, TBX5, HAND2, FOXA1, FOXA2, FOXA3, HNF1α, HNF4α, PAX3 and PAX7. In some preferred embodiments, wherein said Exogenous mRNA encodes OCT3/4, SOX2, KLF4, NANOG, LIN28, and at least one MYC protein selected from c-MYC, c-MYC(T58A) and L-MYC that is repeatedly transfected into a cell comprising said cell, tissue or organism once per day (at a total daily dose of about 0.6-1.2 µg per approximately $10^5$ cells (together with said Agent mRNA) for approximately 15-20 days, said cell is reprogrammed from a somatic cell (e.g., a fibroblast or keratinocyte) to an iPS cell. In some other preferred embodiments, wherein said Exogenous mRNA encodes MYOD1 that is repeatedly transfected into a cell comprising said cell, tissue or organism once per day for at least two days (e.g., at a total daily dose and in conjunction with the Agent mRNA as shown in the Examples herein), said cell is reprogrammed (e.g., differentiated or transdifferentiated) from a mesenchymal stem cell or a somatic cell to a myoblast cell. In still other embodiments, said transfection of said cell with said Exogenous mRNA (in conjunction with the Agent mRNA) results in transdifferentiation of one cell type into a second cell type, or differentiation of an iPSC, embryonic stem cell, or lineage-restricted stem cell into one or more specific downsteam lineages.

In certain embodiments, the transfecting of Exogenous RNA is conducted within 24 hours of the introducing of the Agent mRNA (e.g., from 1-24 hours after the introducing or from 2-15 hours from the introducing). In certain embodiments, the agent is mRNA in introduced at a level between 0.1 and 3.5 µg/ml (e.g., 0.1 . . . 0.9 . . . 1.3 . . . 1.7 . . . 2.3 . . . 2.7 . . . 3.0 . . . 3.3 . . . or 3.5 µg/ml). In additional embodiments, the Agent mRNA is introduced to the cells at a level between 0.1 and 0.8 µg/ml. In particular embodiments, the cell is present in a medium, and the Agent mRNA results in synthesis of protein that is present in said medium. In further embodiments, the Agent mRNA results in synthesis of protein that is present in the medium at a level between 50 and 400 ng/ml (e.g., 50 . . . 100 . . . 150 . . . 200 . . . 250 . . . 300 . . . 350 . . . or 400 ng/ml). In further embodiments, the Agent mRNA results in synthesis of protein that is present in said medium at a level between 100 and 300 ng/ml or about 200 ng/ml (e.g., 100 . . . 130 . . . 170 . . . 200 . . . 245 . . . 275 . . . or 300 ng/ml).

BRIEF DESCRIPTION OF THE FIGURES

The following figures form part of the present specification and are included as examples to further demonstrate certain aspects of the present invention. The invention may be better understood by reference to one or more of these figures in combination with the detailed description of specific embodiments presented herein, but are not intended to limit the invention.

In FIG. 6.A), 0.2 µg/ml of Exogenous mRNA comprising ALKP mRNA was transfected into mouse C3H10T1/2 mesenchymal stem cells, either alone or together with an Agent mRNA comprising 0.5 µg/ml of E3L mRNA, K3L mRNA, or both E3L and K3L mRNAs (each at 0.5 n/ml), or with 0.5 µg/ml of EGFP mRNA as a negative control for the Agent mRNA comprising E3L or K3L mRNA. In FIG. 6.B), 0.2 µg/ml of Exogenous mRNA comprising ALKP mRNA was transfected into human 1079 foreskin fibroblasts, either alone or together with an Agent mRNA comprising 0.5 µg/ml of E3L mRNA, K3L mRNA, or both E3L and K3L mRNAs (each at 0.5 µg/ml), or with 0.5 µg/ml of EGFP as a negative control for the Agent mRNA comprising E3L or K3L mRNA. Cells were lysed and ALKP reporter assays were performed 18 hours post transfection (A, B).

FIG. 8.A) shows untreated C3H10T1/2 cells. FIG. 8.B) shows mock-transfected cells. FIG. 8.C) shows cells transfected with only MYOD mRNA. FIG. 8.D) shows cells co-transfected twice with MYOD mRNAcells+ EGFP mRNA (0.5 µg/ml) as a negative control in place of an Agent mRNA. FIG. 8.E) shows cells co-transfected twice with MYOD mRNA+an Agent mRNA comprising E3L mRNA. FIG. 8.F) shows cells co-transfected twice with MYOD mRNA+an Agent mRNA comprising K3L mRNA. FIG. 8.G) shows cells co-transfected twice with MYOD mRNA+E3L and K3L mRNA.

FIG. 9 shows: (A) the nucleic acid sequence of B18R mRNA (SEQ ID NO:2) and (B) the amino acid sequence of B18R protein (SEQ ID NO:3).

FIG. 10 shows: (A) the nucleic acid sequence of E3L mRNA (SEQ ID NO:4) and (B) the amino acid sequence of E3L protein (SEQ ID NO:5).

FIG. 11 shows: (A) the nucleic acid sequence of K3L mRNA (SEQ ID NO:6) and (B) the amino acid sequence of K3L protein (SEQ ID NO:7).

DETAILED DESCRIPTION OF THE INVENTION

Figure 1:
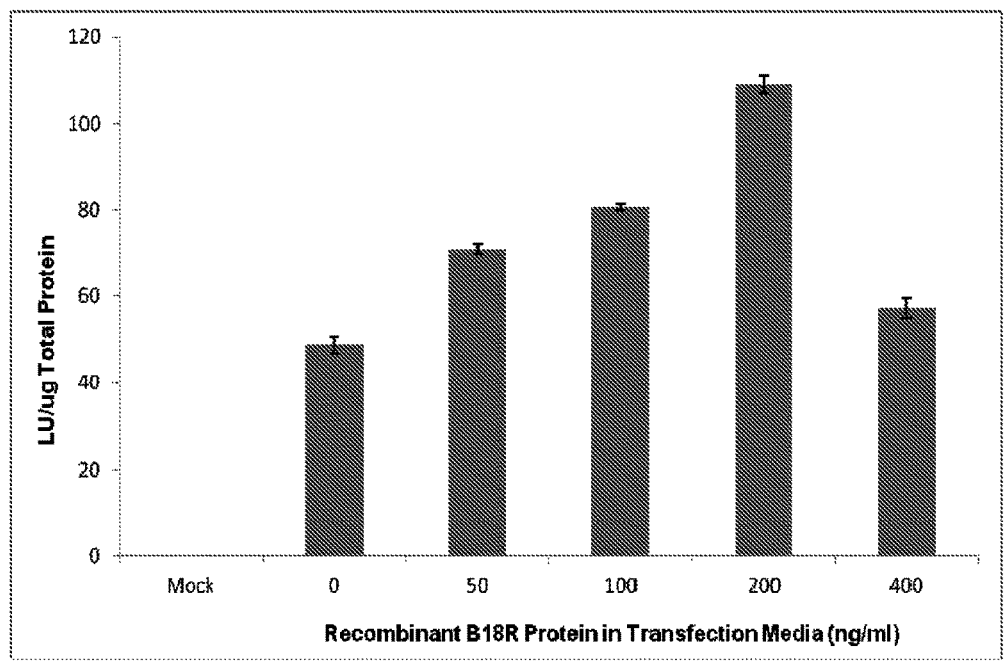
FIG. 1 shows that purified recombinant B18R protein added to the transfection medium increases expression of transfected Exogenous firefly luciferase mRNA. Firefly luciferase mRNA was transfected into BJ fibroblast cells in medium containing various concentrations of purified recombinant B18R protein. Cells were lysed and luciferase activity in light units per microgram (LU/µg) of total protein was measured 20 hours after the luciferase mRNA transfection.

The present invention provides methods, kits, and compositions for increasing translation of Exogenous mRNA in cells using an Agent mRNA that reduces or suppresses an innate immune response induced, for example, by the introduction of Exogenous mRNA. In certain embodiments, the Agent mRNA encodes a protein that inhibits or reduces type I interferon-induced cellular toxicity and/or inhibition of translation resulting from the introduction of Exogenous mRNA into a human or animal cell.

DEFINITIONS AND GENERAL ASPECTS OF THE INVENTION

If the same terms or similar terms have been used with different meaning by others, including those cited in the section entitled "Background" herein, the terms when used to describe the present invention, shall nevertheless be interpreted to have the meanings presented below and in the sections related to the specification and claims, unless otherwise expressly stated to the contrary.

When used in describing an aspect of the present invention, the terms "such as," "including," "for example," "e.g.," and the like shall be interpreted to mean "without limitation."

As used herein, an "Agent mRNA" means in vitro-synthesized mRNA encoding one or more proteins that affect the induction, activity or response of an innate immune response pathway, whereby the innate immune response in a cell (e.g., a cell in a tissue or organism) is reduced, suppressed or prevented compared to the innate immune response in the absence of introducing said in vitro-synthesized mRNA.

As used herein, "Exogenous RNA" means RNA that is synthesized in an in vitro transcription reaction by an RNA polymerase using a DNA template that exhibits an RNA polymerase promoter sequence recognized by said RNA polymerase upstream of a DNA sequence encoding the sequence of an RNA which is desired to cause a biological or medical effect, which effect does not include functioning as an Agent mRNA, and wherein said RNA induces an innate immune response upon introduction into a cell, tissue or organism; "Exogenous RNA" includes, for example, RNA that exhibits a sequence encoding at least one protein and which is capable of being translated into protein upon introduction into a living cell that has a functional translation system, and also includes RNA that exhibits an mRNA cap structure and a poly(A) tail. "Exogenous RNA" may also include-undesired RNA molecules that are synthesized in the in vitro transcription reaction, including truncated RNA due to abortive transcription or incomplete synthesis, uncapped in vitro transcription products, and dsRNA. In some cases herein, we refer to Exogenous RNA which encodes at least one protein (e.g., one or more proteins), including wherein the Exogenous RNA exhibits a cap structure and a poly(A) tail, as "Exogenous mRNA." One important benefit of the methods, kits and compositions of the present invention is that the Agent mRNA reduces or suppresses an innate immune response which would be induced by the Exogenous RNA in the absence of such Agent mRNA.

As used herein, "Exogenous siRNA" and "Exogenous miRNA" mean a siRNA or miRNA, respectively, that is synthesized in vitro using any method known in the art, and that is for the purpose of causing a biological or medical effect in a cell, tissue or organism into which it is introduced, which effect does not include functioning as an Agent mRNA. In some embodiments, the Exogenous miRNA or Exogenous siRNA is synthesized by in vitro transcription of a DNA template, including in either one or two in vitro transcription reactions using either one or two DNA templates or one RNA polymerase that recognizes one RNA polymerase promoter sequence or two different RNA polymerases, each or which recognizes a different RNA polymerase promoter sequence, or by chemical synthesis on an oligonucleotide synthesizer using methods known in the art.

Agent mRNA and Exogenous RNA (e.g., mRNA) can be made using similar methods. For example, in some embodiments of the methods, kits, systems or compositions of the invention, the Agent mRNA or Exogenous RNA, or other RNA, is synthesized by in vitro transcription (IVT) of a DNA template using an RNA polymerase (e.g., SP6, T3 or T7 RNA polymerase) and nucleoside-5'-triphosphates (NTPs). In some embodiments, the NTPs used for IVT comprise or consist of only GTP ATP, UTP, and CTP ("canonical NTPs"), and the Agent mRNA or Exogenous RNA product is described as "GAUC." In other embodiments, a modified NTP is used in place of some or all of one or more of the respective canonical NTPs. In some preferred embodiments, the modified NTP, pseudouridine-5'-triphosphate (ψTP) is used for IVT in place of some or all of the UTP; if ψTP is used for IVT in place of all of the UTP, the Agent mRNA or Exogenous RNA product is described as "GAψC." In some preferred embodiments, the modified NTP, 5-methylcytidine-5'-triphosphate (m$^5$CTP or 5mCTP)

is used for IVT in place of some or all of the CTP. In some preferred embodiments wherein ψTP is used for IVT in place of some or all of the UTP, m⁵CTP is also used in place of some or all of the CTP. In some preferred embodiments, both ψTP and m⁵CTP are used for IVT in place of all of the corresponding UTP and CTP, and the Exogenous RNA product is described as "GAψm⁵C" or "GAψ5mC." In most embodiments, the Agent mRNA or Exogenous RNA is mRNA, meaning that it exhibits a "cap" on its 5'-terminus and a poly(A) tail on its 3'-terminus, as will be generally understood by those with knowledge in the art. In some preferred embodiments, Agent mRNA or Exogenous RNA that is mRNA is synthesized by IVT, followed by addition of the cap using a capping enzyme system comprising RNA guanyltransferase activity and addition of a poly(A) tail using a poly(A) polymerase (e.g., using an T7 mScript™ Standard mRNA Production System, as described elsewhere herein). In some other embodiments, the cap is added by incorporation of a dinucleotide cap analog (e.g., m7GpppG or the 3'-O-methyl-m7GpppG ARCA) during IVT. In some embodiments, the poly(A) tail is added to the 3'-terminus during IVT of a DNA template that encodes the poly(A) tail.

In some preferred embodiments of the methods, kits, systems and compositions, the Agent mRNA, Exogenous RNA (e.g., Exogenous mRNA), Exogenous miRNA or Exogenous siRNA comprises or consists of GAψC RNA. In other preferred embodiments of the methods, kits, systems and compositions, the Agent mRNA, Exogenous RNA (e.g., Exogenous mRNA), Exogenous miRNA or Exogenous siRNA comprises or consists of GAψm⁵C RNA.

In some preferred embodiments, Agent mRNA is further purified. In some embodiments, Exogenous RNA (e.g., Exogenous mRNA) is also further purified, in which embodiments, the same purification methods, purity quality standards, and assays for purity, as described herein may be used. In certain embodiments, the Agent mRNA is purified so that the mRNA is substantially free, virtually free, essentially free, or free of contaminants (or of a particular RNA contaminant, such as dsRNA). By "substantially free," "virtually free," "essentially free," or "free" of contaminants (or of a particular RNA contaminant, such as dsRNA), it is meant that less than 0.5%, less than 0.1%, less than 0.05%, or less than 0.01%, respectively, of the total mass or weight of the RNA in the Agent mRNA is composed of contaminants (or of a particular RNA contaminant, such as dsRNA). The amounts and relative amounts of non-contaminant mRNA molecules and RNA contaminant molecules (or of a particular RNA contaminant, such as dsRNA) may be determined by HPLC or other methods used in the art to separate and quantify RNA molecules. In some preferred embodiments wherein the Agent mRNA (including GAUC, GAψC or GAψm⁵C Agent mRNA) is substantially free, virtually free, essentially free, or free of contaminant dsRNA, the relative amounts of non-contaminant mRNA and of contaminant dsRNA are assayed using the J2 dsRNA-specific antibody (English & Scientific Consulting, Szirak, Hungary); by "substantially free," "virtually free," "essentially free," or "free" of dsRNA it is meant that less than 0.5%, less than 0.1%, less than 0.05%, or less than 0.01%, respectively, of the total mass or weight of the RNA in the Agent mRNA consists of dsRNA of a size greater than about 40-basepairs in length when assayed by dot blot immunoassay as described below using the J2 dsRNA-specific antibody or using another assay that gives equivalent results to the assay described herein. It shall be understood herein that the results of the dot blot immunoassays using the J2 dsRNA-specific antibody will be based on comparing the assay results obtained using the Agent mRNA with the assay results of J2 dsRNA-specific antibody dot blot immunoassays performed at the same time with dsRNA standards comprising known quantities of dsRNA of the same or equivalent size and J2 antibody binding.

As defined herein, Agent mRNA (or Exogenous mRNA) may be analyzed for the amount or relative amount of contaminant dsRNA by performing the following dot blot immunoassay using a dsRNA-specific antibody, such as the J2 dsRNA-specific antibody, or another antibody that gives equivalent results: RNA samples are spotted (5 μl/dot) on Nytran SPC positively charged nylon membranes and then allowed to dry on the nylon membrane for 30 minutes. The membrane is then blocked in blocking buffer (25 mM Tris, pH 7.5, 150 mM NaCl, 0.05% Tween 20, 5% W/V dry milk) at room temperature for 1 hour on a rotating platform. The primary antibody (e.g., J2 antibody; English & Scientific Consulting, Hungary) is added at 1 μg/ml in blocking buffer at room temperature for 1 hour on a rotating platform. The membranes are then washed 6 times for 5 minutes in 20 mls of wash buffer (25 mM Tris, pH 7.5, 150 mM NaCl, 0.05% Tween 20). The secondary antibody (anti-mouse HRP (Cell Signaling Technologies, Danvers, Mass.) is added at 1:1000 in blocking buffer at room temperature for 1 hour on a rotating platform. The membranes are then washed 6 times for 5 minutes in 20 mls of wash buffer (25 mM Tris, pH 7.5, 150 mM NaCl, 0.05% Tween 20). Then, equal volumes of Supersignal West Pico Chemiluminescent Substrates (Cat #34080, Thermo Scientific) are added and the color is allowed to develop for 5 minutes on a rotating platform. The dots are imaged by exposing film in the dark room and developing the film in Kodak Developer for 1 minute and Kodak Fixer for 1 minute.

The present invention is not limited with respect to the purification methods used to purify the Agent mRNA or Exogenous mRNA, and the invention includes use of any method that is known in the art or developed in the future in order to purify the mRNA and remove contaminants, including RNA contaminants, that interfere with the intended use of the mRNA. For example, in preferred embodiments, the purification of the mRNA removes contaminants that are toxic to the cells (e.g., by inducing an innate immune response in the cells, or, in the case of RNA contaminants comprising dsRNA, by inducing an interferon response or by inducing RNA interference (RNAi), e.g., (via siRNA, miRNA or long RNAi molecules) and contaminants that directly or indirectly decrease translation of the mRNA in the cells. In some embodiments, the mRNA is purified by HPLC. In certain embodiments, the mRNA is purified using on a polymeric resin substrate comprising a C18 derivatized styrene-divinylbenzene copolymer and a triethylamine acetate (TEAA) ion pairing agent is used in the column buffer along with the use of an acetonitrile gradient to elute the mRNA and separate it from the RNA contaminants in a size-dependent manner; in some embodiments, the mRNA purification is performed using HPLC, but in some other embodiments a gravity flow column is used for the purification. In some embodiments, the mRNA is purified using a method described in the book entitled "RNA Purification and Analysis" (Gjerde et al., 2009). In some embodiments, the mRNA purification is carried out in a non-denaturing mode (e.g., at a temperature less than about 50° C., e.g., at ambient temperature). In some embodiments, the mRNA purification is carried out in a partially denaturing mode (e.g., at a temperature less than about 50° C. and 72° C.). In some embodiments, the mRNA purification is carried out in a denaturing mode (e.g., at a temperature greater than about 72° C.). Those with knowledge in the art will know that the denaturing temperature depends on the melting temperature (Tm) of the mRNA that is being purified as well as on the melting temperatures of RNA, DNA, or RNA/DNA hybrids which contaminate the mRNA. In some other embodiments, the mRNA is purified as described (Mellits et al., 1990). These authors used a three step purification to remove the contaminants which may be used in embodiments of the present invention. Step 1 was 8% polyacrylamide gel electrophoresis in 7M urea (denaturing conditions). The major RNA band was excised from the gel slice and subjected to 8% polyacrylamide gel electrophoresis under nondenaturing condition (no urea) and the major band recovered from the gel slice. Further purification was done on a cellulose CF-11 column using an ethanol-salt buffer mobile phase which separates double stranded RNA from single stranded RNA (Barber, 1966; Franklin, 1966; Zelcer et al., 1981) and the final purification step was cellulose chromatography. In some other embodiments, the mRNA is purified using an hydroxylapatite (HAP) column under either non-denaturing conditions or at higher temperatures as described in (Andrews-Pfannkoch et al., 2010; Clawson and Smuckler, 1982; Lewandowski et al., 1971; Pays, 1977). In some other embodiments, the mRNA is purified by weak anion exchange liquid chromatography under non-denaturing conditions as described by (Easton et al., 2010). In some embodiments, the mRNA is purified using a combination of any of the above methods or another method known in the art or developed in the future. In still another embodiment, the mRNA used in the compositions and methods of the present invention is purified using a process which comprises treating the mRNA with an enzyme that specifically acts on (e.g., digests) one or more contaminant RNA or contaminant nucleic acids (e.g., including DNA), but which does not act on (e.g., does not digest) the desired mRNA. For example, in some embodiments, the mRNA used in the compositions and methods of the present invention is purified using a process which comprises treating the mRNA with a ribonuclease III (RNase III) enzyme (e.g., *E. coli* RNase III) and the mRNA is then purified away from the RNase III digestion products. A ribonuclease III (RNase III) enzyme herein means an enzyme that digests dsRNA greater than about twelve basepairs to short dsRNA fragments. In some embodiments, the mRNA used in the compositions, kits and methods of the present invention is purified using a process which comprises treating the mRNA with one or more other enzymes that specifically digest one or more contaminant RNAs (e.g., dsRNA) or contaminant nucleic acids (e.g., including DNA).

"Differentiation" or "cellular differentiation" means the naturally occurring biological process by which a cell that exhibits a less specialized state of differentiation or cell type (e.g., a fertilized egg cell, a cell in an embryo, or a cell in a eukaryotic organism) becomes a cell that exhibits a more specialized state of differentiation or cell type. Scientists, including biologists, cell biologists, immunologists, and embryologists, use a variety of methods and criteria to define, describe, or categorize different cells according to their "cell type," "differentiated state," or "state of differentiation." In general, a cell is defined, described, or categorized with respect to its "cell type," "differentiated state," or "state of differentiation" based on one or more phenotypes exhibited by that cell, which phenotypes can include shape, a biochemical or metabolic activity or function, the presence of certain biomolecules in the cell (e.g., based on stains that react with specific biomolecules), or on or in the cell (e.g., based on binding of one or more antibodies that react with specific biomolecules inside the cell or on the cell surface). For example, in some embodiments, different cell types are identified and sorted using a cell sorter or fluorescent-activated cell sorter (FACS) instrument. "Differentiation" or "cellular differentiation" can also occur to cells in culture. In some embodiments, the term "reprogramming" is used herein to refer to differentiation or cellular differentiation, including de-differentiation or transdifferentiation, that occurs in response to delivery of one or more reprogramming factors into the cell, directly (e.g., by delivery of protein or polypeptide reprogramming factors into the cell) or indirectly (e.g., by delivery of an exogenous RNA preparation of the present invention which consists of one or more mRNA molecules, each of which encodes a reprogramming factor) and maintaining the cells under conditions (e.g., medium, temperature, oxygen and $CO_2$ levels, matrix, and other environmental conditions) that are conducive for differentiation. The term "reprogramming" when used herein is not intended to mean or refer to a specific direction or path of differentiation (e.g., from a less specialized cell type to a more specialized cell type) and does not exclude processes that proceed in a direction or path of differentiation than what is normally observed in nature. Thus, in different embodiments of the present invention, "reprogramming" means and includes any and all of the following:

(1) "Dedifferentiation", meaning a process of a cell that exhibits a more specialized state of differentiation or cell type (e.g., a mammalian fibroblast, a keratinocyte, a muscle cell, or a neural cell) going to a cell that exhibits a less specialized state of differentiation or cell type (e.g., an iPS cell);

(2) "Transdifferentiation", meaning a process of a cell that exhibits one specialized state of differentiation or cell type (e.g., a mammalian fibroblast, a keratinocyte, or a neural cell) going to a different specialized state of differentiation or cell type (e.g., from a fibroblast or keratinocyte to a muscle cell); and (3) "Expected or Natural Differentiation", meaning a process of a cell that exhibits any particular state of differentiation or cell type going to another state of differentiation or cell type as would be expected in nature if the cell was present in its natural place (e.g., in an embryo or an organism).

In some embodiments, the Agent mRNAs in the methods, compositions, systems, and kits of the present invention comprise or consist of the B18R, E3L, and K3L mRNAs that exhibit the nucleic acid sequences in FIGS. 9A-11A or that encode proteins that exhibit the amino acid sequences in FIGS. 9B-11B, as well as mRNAs that exhibit nucleic acid sequences or encode protein sequences that are variant sequences that are substantially the same as those nucleic acid sequences or amino acid sequences. For example, one, two, or more bases in one, two, or more codons may be changed in the nucleic acid sequence (or one, two or more amino acids may be changed in the amino acid sequence) such that a sequence differing from a sequence shown in any of FIGS. 9-11 is generated. Changes to the amino acid sequence may be generated by changing the nucleic acid sequence encoding the amino acid sequence. For example, the mRNA encoding a variant of B18R, E3L, or K3L protein may be prepared by methods known in the art using the guidance of the present specification for particular sequences. These methods include, but are not limited to, preparation by site-directed (or oligonucleotide-mediated) mutagenesis, PCR mutagenesis, and cassette mutagenesis of an earlier prepared DNA template used for in vitro transcription (IVT) of mRNA encoding a B18R, E3L, or K3L protein. Site-directed mutagenesis is a preferred method for preparing substitution variants. This technique is well known in the art (Carter et al., 1985; Kunkel, 1985).

Briefly, in carrying out site directed mutagenesis of a DNA template, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated into the resulting double-stranded DNA.

PCR mutagenesis is also suitable for making nucleic acid or amino acid sequence variants in the DNA template that is used for IVT (Vallette et al., 1989). Briefly, a small amount of the starting DNA template that one wishes to mutate is amplified by PCR using at least one PCR primer that exhibits a desired variant nucleic acid sequence compared to the corresponding region in the starting DNA template to generate a relatively large quantity of a specific DNA fragment that differs from the starting DNA template sequence only at the positions where the at least one PCR primers differed from the starting DNA template. This PCR mutagenesis process can be repeated using the product of a prior PCR mutagenesis reaction to introduce additional desired mutations in the DNA template.

Another method for preparing sequence variants, known as cassette mutagenesis, is based on the technique described by (Wells et al., 1985). The starting material is the plasmid (or other vector) comprising the starting DNA template to be mutated. The codon(s) in the starting DNA template to be mutated are first identified. There should be a unique restriction endonuclease site on each side of the identified mutation site(s). If no such restriction sites exist, they are generated in the starting DNA template using the above-described oligonucleotide-mediated mutagenesis method. The plasmid DNA is then cut with the restriction enzyme(s) to linearize it at these sites. Two oligonucleotides that exhibit the sequences of each strand of the DNA between the restriction sites but containing the one or more desired mutations are synthesized using standard procedures, and then hybridized together using standard techniques to generate a double-stranded DNA referred to as the cassette. This cassette is designed to have 5' and 3' ends that are compatible with the ends of the linearized plasmid, such that it can be directly ligated into the plasmid DNA from which the corresponding unmutated DNA was removed. This plasmid DNA now contains the mutated DNA sequence and can be used to prepare the DNA template for in vitro transcription of mRNA that exhibits the desired variant sequence.

Alternatively, or additionally, the desired amino acid sequence encoding one or more polypeptide variants can be determined, and a nucleic acid sequence encoding such amino acid sequence variant(s) can be generated synthetically. Conservative modifications in the amino acid sequences of the proteins may also be made. Naturally occurring residues are divided into classes based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Conservative substitutions will entail exchanging a member of one of these classes for another member of the same class.

The expected activity of the variant protein is confirmed following introduction of the Agent mRNA variant (e.g., from in vitro transcription of the variant DNA template) into the cell using methods disclosed herein.

Variant Agent mRNAs that encode variant B18R, E3L, or K3L proteins are generated (e.g., by truncation, deletion, or insertion into the DNA template for IVT) and screened as described in the Examples herein to determine if they function to reduce or suppress the innate immune response induced by a Foreign Substance (e.g., by the introduction of an Exogenous RNA into a cell). In this regard, any variant of an Agent mRNA that is constructed can be screened to identify variants suitable for use as a composition of the present invention or for use in a kit or method of the present invention.

Some embodiments of the invention comprise a kit or composition comprising or consisting of the mRNA encoding the antibody or artificial antibody. In some embodiments of any of the methods, kits and compositions of the invention, the mRNA is Agent mRNA encoding an antibody or artificial antibody. In some embodiments of any of the methods, kits and compositions of the invention, the mRNA is Exogenous mRNA encoding an antibody or artificial antibody.

Still another embodiment of the invention is a composition comprising or consisting of Exogenous mRNA encoding an antibody or artificial antibody for any desired function for which an antibody comprising protein is used in a cell, tissue or organism. For example, in some embodiments, the Exogenous mRNA encodes one or more antibodies or artificial antibodies that binds to a cell-specific or disease-specific or pathogen-specific protein that is expressed in a human or animal cell, tissue or organism. For example, in some embodiments, the Exogenous mRNA encodes one or more antibodies or artificial antibodies that binds to a cancer-specific or tumor-specific protein. In some embodiments of the method, Exogenous mRNA encoding one or more antibodies or artificial antibodies that is or are specific for a condition, disease or pathogen infecting a human or animal patient is administered to the patient to treat the condition, disease or pathogen-induced state (e.g., by administering the Exogenous mRNA to a cell, tissue or organism in the patient, e.g., by transfection, electroporation, or by intravenous, interperitoneal, intradermal, subdermal, or internodal injection). In some embodiments, the sequence of an mRNA encoding an antibody that reduces an innate immune response is first made in a non-human species and then, using any of the methods known in the art, the Agent mRNA in made by modifying the sequence so that the protein encoded by said Agent mRNA is similar to an antibody which would be produced naturally in humans; the antibody encoded by said Agent mRNA is then said to be "humanized" because it is has been adapted to be suitable for use in humans with minimal chance of inducing an active immune response. Agent mRNA encoding antibodies intended for use in other species can be similarly adapted for use in those species.

EXAMPLES

The following examples are provided in order to demonstrate and further illustrate certain preferred embodiments and aspects of the present invention and are not to be construed as limiting the scope thereof.

These examples demonstrate that Agent mRNA comprising or consisting of B18R mRNA, E3L mRNA, and K3L mRNA, alone or in combination, decrease cell toxicity (or increase cell survival) and increase translation of Exogenous mRNAs that are transfected into human or other mammalian cells. For example, introducing these Agent mRNAs into cells at the same time as or prior to (e.g., in some embodiments, 8-24 hours prior to) transfecting the cells with Exogenous mRNAs encoding one or more other proteins of interest enhances the translation or activity of the proteins encoded by those other Exogenous mRNAs. These Examples also demonstrate that introducing these Agent mRNAs into cells inhibits the biological activity of type I interferons (IFNα, IFNβ) but not type II interferons (INFγ). The Examples also demonstrate that introducing Agent mRNAs comprising E3L mRNA, K3L mRNA, or both E3L mRNA and K3L mRNA together with an Exogenous mRNA comprising in vitro-transcribed MYOD mRNA resulted in reprogramming of mouse C3H10T1/2 mesenchymal stem cells to myoblast cells, whereas no reprogramming occurred when the C3H10T1/2 mesenchymal stem cells were transfected only with Exogenous mRNA comprising MYOD mRNA in the absence of these Agent mRNAs.

Materials and Methods

Templates for In Vitro Transcription

A B18R DNA template for preparing Agent mRNA comprising or consisting of B18R mRNA (GAψC) was prepared as follows: a B18R coding sequence (cds) was cloned into a pUC-based plasmid DNA that contained a T7 RNA polymerase promoter followed by 5' Xenopus Beta Globin (UTR), a cloning site (into which the B18R cds was inserted), and a 3' Xenopus Beta Globin 3' UTR, and then linearized with NotI.

An E3L DNA template for preparing Agent mRNA comprising or consisting of E3L mRNA (GAψm$^5$C) was prepared as follows: an E3L cds was cloned into a pUC19-based plasmid DNA that contained a T7 RNA polymerase promoter followed by 5' Xenopus Beta Globin (UTR), a cloning site (into which the E3L cds was inserted), and a 3' Xenopus Beta Globin 3' UTR, and then linearized with SalI.

A K3L DNA template for preparing Agent mRNA comprising or consisting of K3L mRNA (GAψm$^5$C) was prepared as follows: a K3L cds was cloned into a pUC19-based plasmid DNA that contained a T7 RNA polymerase promoter followed by 5' Xenopus Beta Globin (UTR), a cloning site (into which the K3L cds was inserted), and a 3' Xenopus Beta Globin 3' UTR, and then linearized with SalI.

EGFP and c-MYC DNA templates for preparing EGFP or c-MYC mRNA (GAψm$^5$C), respectively, for use as negative control mRNAs in place of Agent B18R, E3L or K3L mRNAs, were prepared as follows: the respective EGFP or c-MYC cds was cloned into a pUC19-based plasmid DNA that contained a T7 RNA polymerase promoter followed by 5' Xenopus Beta Globin (UTR), a cloning site (into which the respective cds was inserted), and a 3' Xenopus Beta Globin 3' UTR, and then linearized with SalI.

A mouse Alkaline Phosphatase (ALKP) DNA template for preparing Exogenous mRNA comprising or consisting of mouse ALKP mRNA (GAUC) was prepared as follows: the mouse ALKP cds was cloned into a pUC19-based plasmid DNA that contained a T7 RNA polymerase promoter followed by 5' Xenopus Beta Globin (UTR), a cloning site (into which the mouse ALKP cds was inserted), and a 3' Xenopus Beta Globin 3' UTR, and then linearized with SalI.

A mouse MYOD DNA template for preparing mouse Exogenous mRNA comprising or consisting of mouse MYOD mRNA (GAUC) for use in reprogramming mouse mesenchymal stem cells or somatic cells (e.g., fibroblasts) to myoblast cells was prepared as follows: the MYOD cds was cloned into a pUC19-based plasmid DNA that contained a T7 RNA polymerase promoter followed by 5' Xenopus Beta Globin (UTR), a cloning site (into which the MYOD cds was inserted), and a 3' Xenopus Beta Globin 3' UTR, and then linearized with SalI.

A luciferase (luc2) DNA template for preparing Exogenous mRNA comprising or consisting of firefly luciferase luc2 (Photinus pyralis luc2) mRNA (GAUC) was obtained by linearizing a commercially available plasmid (Promega, Madison, Wis.).

DNA templates for preparing other Exogenous mRNAs are similarly prepared as follows: the cds is cloned into a pUC19-based plasmid DNA that contains a T7 RNA polymerase promoter followed by 5' Xenopus Beta Globin (UTR), a cloning site (into which the cds is inserted), and a 3' Xenopus Beta Globin 3' UTR, and then linearized with SalI (or another restriction enzyme if the cds contains a SalI restriction site). For example, DNA templates were thus prepared for use in making mRNAs encoding the human and mouse transcription factors OCT4, SOX2, KLF4, LIN28, NANOG, c-MYC, L-MYC, and c-MYC(T58A), and Exogenous mRNAs are prepared using these templates as described herein, and used for reprogramming somatic cells to pluripotent stem cells. For example, in some embodiments, a total of about 1 to 1.2 microgram per transfection of mRNAs encoding human or mouse OCT4, SOX 2, KLF4 and a MYC protein selected from c-MYC, L-MYC and c-MYC(T58A) at a ratio of 3:1:1-3:1, respectively, (or 1 to 1.2 microgram per transfection of mRNAs encoding human or mouse OCT4, SOX 2, KLF4 and a MYC protein selected from c-MYC, L-MYC and c-MYC(T58A), and LIN28 and/or NANOG at a ratio of 3:1:1-3:1:1:(1) are transfected into human or animal somatic cells once daily for about 18 days, whereby the somatic cells are reprogrammed to pluripotent stem cells. In some embodiments, the use of an Agent mRNA encoding B18R, E3L and/or K3L proteins, or encoding other proteins inhibitors of innate immune response that are disclosed herein, facilitates or enhances the reprogramming of somatic cells to pluripotent stem cells by these Exogenous mRNAs. In still other embodiments, said Agent mRNA facilitates or enhances the reprogramming (e.g., differentiation, transdifferentiation) of one type of cell to another type of cell).

In Vitro Transcription, Capping and Polyadenylation to Make mRNAs

Each of the mRNAs used for transfection in the various experiments was prepared by in vitro transcription of the respective linear DNA template using the in vitro transcription components, the capping enzyme components, and the polyadenylation components provided in a T7 mScript™ Standard mRNA Production System (or the IVT components of an INCOGNITO™ T7 Ψ-RNA Transcription Kit or an INCOGNITO™ T7 5mC- & Ψ-RNA Transcription Kit) as described by the manufacturer (CELLSCRIPT, Inc., Madison, Wis.) unless otherwise stated herein. In some experiments in which a T7 mScript™ Standard mRNA Production System was used, pseudouridine triphosphate (ΨTP) and/or m$^5$CTP was used for in vitro transcription instead the corresponding UTP or CTP, respectively. The DNA templates for in vitro transcription were prepared as generally described in the T7 mScript™ or INCOGNITO™ product literature (e.g., by linearization of plasmid containing the mRNA coding sequence or by PCR of said gene).

NotI-linearized B18R DNA template was used as a template in in vitro transcription reactions using either the INCOGNITO™ T7 μl-RNA Transcription Kit, which contains pseudouridine triphosphate (ΨTP) instead of UTP (CELLSCRIPT, Inc.), or the in vitro transcription components in the T7 mScript™ Standard mRNA Production System, except that ΨTP was used in place of the UTP, to generate GAΨC RNA, which was subsequently capped and tailed to make GAΨC mRNA.

E3L or K3L DNA templates were used as templates in in vitro transcription reactions containing ΨTP and m⁵CTP to generate GAΨm⁵C RNAs, which were subsequently capped and tailed to make GAΨm⁵C mRNAs. Similarly, in some experiments, EGFP RNA or c-MYC mRNA was made for use as a negative control in place of Agent B18R, E3L or K3L mRNA by in vitro transcription of the respective linearized DNA template using either an INCOGNITO™ T7 5mC- & Ψ-RNA Transcription Kit (CELLSCRIPT, Inc.), which contains m⁵CTP and ΨTP, or the T7 mScript™ Standard mRNA Production System, but with m⁵CTP (Trilink, San Diego, Calif.) and ΨTP in place of standard CTP and UTP, respectively; these were subsequently capped and tailed to make GAΨm⁵C mRNAs.

Prior to capping and poly(A) tailing, Agent mRNAs E3L mRNA and K3L mRNA, as well as EGFP and c-MYC mRNAs, which were used as negative controls in place of Agent mRNA in the Examples herein, were treated with RNase III to remove interferon-inducing dsRNA, as described in the literature provided with the MINiMMU-NET™ Kit (CELLSCRIPT, Inc).

All mRNAs used herein as Exogenous mRNAs that were not Agent mRNAs for inhibiting an innate immune response or control mRNAs for replacing an agent comprising mRNA for inhibiting an innate immune response were made by in vitro transcription of the respective DNA templates using the IVT components of the T7 mScript™ Standard mRNA Production System and only the canonical nucleotides GTP, ATP, UTP and CTP (GAUC). For example, firefly luciferase luc2 mRNA and mouse ALKP mRNA, which were used as Exogenous mRNAs for expressing proteins in cells whose activities could be easily detected and quantified, and MYOD mRNA, which was used as Exogenous mRNAs for expression in cells in order to induce reprogramming of the cells to myoblasts, were made by in vitro transcription of the respective DNA templates using the IVT components of the T7 mScript™ Standard mRNA Production System and only the canonical nucleotides GTP, ATP, UTP and CTP to generate GAUC RNA. For example, in some experiments, firefly luciferase luc2 (Photinus pyralis luc2) RNA was made for use as Exogenous mRNA by in vitro transcription of a linearized plasmid (Promega, Madison, Wis.) with only GTP, ATP, UTP and CTP (i.e., without substitution by ΨTP or m⁵CTP). The Exogenous mRNAs containing GAUC disclosed herein are solely for the purpose of examples and are not intended to limit the application of the methods, compositions or kits disclosed herein. For example, in other embodiments, these Exogenous mRNAs are made by in vitro transcription using ΨTP in place of UTP, and in still other embodiments, the Exogenous mRNAs are made by in vitro transcription using m⁵CTP in place of CTP, including wherein ΨTP is used in place of UTP.

In order to make mRNA, in vitro-transcribed RNAs are capped using the ScriptCap™ m⁷G Capping Enzyme System (CELLSCRIPT, Inc.) to make cap0 RNA or using both the ScriptCap™ m⁷G Capping Enzyme System and the ScriptCap™ 2'-O-Methyltransferase (CELLSCRIPT, Inc.) to make cap1 RNA, or with the same capping enzyme components in the T7 mScript™ Standard mRNA Production System; unless otherwise stated herein, all of the capped mRNAs used in the Examples herein exhibited a cap1 structure. For example, B18R RNA was capped with the ScriptCap™ m⁷G Capping Enzyme System and Script-Cap™ 2'-O-Methyltransferase (CELLSCRIPT, Inc.) or with the corresponding capping enzyme components in the T7 mScript™ Standard mRNA Production System, as described in the respective product literature.

The resulting capped RNAs were polyadenylated using either the A-Plus™ Poly(A) Polymerase Tailing Kit (CELLSCRIPT, Inc.) or the poly(A) tailing components of the T7 mScript™ Standard mRNA Production System, as described in the respective product literature. For example, the resulting Cap 1-capped B18R RNA was polyadenylated using either the A-Plus™ Poly(A) Polymerase Tailing Kit or the poly(A) tailing components of the T7 mScript™ Standard mRNA Production System to generate B18R mRNA. For example, a 30-minute reaction using the A-Plus™ Poly(A) Polymerase Tailing Kit generated mRNAs with a poly(A) tail comprising approximately 150 A residues.

The in vitro-transcribed and capped and poly(A)-tailed Agent mRNAs or Exogenous mRNAs were made and purified as described in the literature provided with the T7 mScript™ Standard mRNA Production System. Briefly, after completion of the IVT reaction, the DNA template for IVT was digested by adding RNase-free DNase I to the in vitro transcription reaction and incubating for 15 minutes at 37° C. Then, the RNA was phenol-chloroform extracted, then precipitated by adding an equal volume of 5M ammonium acetate, incubated on ice for 10 minutes and spinning at 13,000 rpms for 10 minutes. The RNA pellet was washed with 70% ethanol and dissolved in water. Following capping and poly(A) tailing, the mRNA was again phenol-chloroform extracted, precipitated with ammonium acetate, washed with 70% ethanol and dissolved in water.

mRNA Transfections

Transfections were performed using commercially available transfection reagents, including the TransIT™ mRNA transfection reagent (Minis Biosciences) and RNAiMax™ (Invitrogen), as described in the manufacturers' literature. For example,
for TransIT™, the RNA was diluted in 250 μls Opti-MEMI (Invitrogen) and mixed with 5 μls TransIT™ BOOST reagent and 5 μs TransIT™ transfection reagent and the mixture was immediately applied to the cells. The present invention is not limited to use of these transfection reagents for delivering the Agent mRNA into cells. Any reagent or method (e.g., electroporation) that results in efficient delivery of the Agent mRNA into the cells and that does not result in high toxicity can be used in or with the compositions, kits or methods of the present invention.

Luciferase Assays

In all experiments with firefly luciferase luc2, except the pre-treatment time course, cells were washed in 2 mls 1×PBS and incubated with 500 μls 1× Reporter Lysis Buffer (Promega). Plates were frozen for at least 1 hour, as the buffer requires a freeze-thaw cycle, and thawed at room temperature. Lysates were then transferred into microcentrifuge tubes and activity was determined using the Luciferase Assay System (Promega), where 20 μls of lysate was incubated with 100 μls of the kit luciferase reagent. Light emission was measured for 10 seconds with no lag time on a Lumiskan™ Ascent luminometer (Thermo Scientific). Protein concentration was determined for lysate samples using the Pierce BCA Protein Assay Kit (Fisher) and used to determine the total amount of protein present in 20 μls of lysate. Luminescence readings were normalized to the amount of protein used for the luciferase assays. In the pre-treatment time course experiment, cells were lysed using 1× Passive Lysis Buffer (Promega), in which a freeze thaw cycle was not required. Cells in these experiments were washed with 2 mls 1×PBS, incubated with 500 µls 1× Passive Lysis Buffer for 2 minutes at room temperature, and transferred to microcentrifuge tubes. The lysate was then used in activity assays as described above.

Assays of the Effects of Purified B18R Protein on Expression of Exogenous Luciferase mRNA BJ fibroblasts (ATCC) were plated onto 6-well dishes coated with 0.1% gelatin (Millipore) at 1×10$^5$ cells per well. Cells were fed fibroblast media consisting of Advanced MEM (Invitrogen), 10% Hyclone Heat Inactivated FBS (Fisher), 2 mM GLUTAMAX™ (Invitrogen), and 0.1 mM beta-mercaptoethanol (Sigma). Purified B18R protein (eBiosciences) was added to make final concentrations of 0, 50, 100, 200 or 400 ng/ml. Cells were transfected with luciferase mRNA at a final concentration of 1.4 µg/ml as described above. After 20 hours, cells were lysed and assayed for luciferase activity as described above.

Assays for Effects of B18R-Conditioned Medium on Luciferase Expression

Either BJ or 1079 fibroblast cells (both from ATCC) were plated 1×10$^5$ cells per well in a 6-well dish coated with 0.1% gelatin. Both cell types were transfected with a plasmid that expresses the B18R protein under control of the constitutive CMV promoter at a final concentration of 2.7 µg/ml using Lipofectamine™ 2000 (Invitrogen). A control plasmid that expressed EGFP under control of the CMV promoter was co-transfected at 0.5 µg per reaction to check how well the transfection procedure worked. In the DNA transfections, 0.5 µl of Lipofectamine 2000 per mg of DNA was mixed with 12.5 µls per mg DNA of Opti-MEMI and incubated at room temperature for 5 minutes. The mixture was then added to a solution of the DNA plus 12.5 µls per µgs of DNA of Opti-MEMI. The transfection mix was incubated at room temperature for 20 minutes before application to cells fed with 1.5 mls of fibroblast media. Transfection medium was removed 4 to 5 hours after transfection, and cells were fed with 2.5 mls fresh fibroblast media per well. In the case of 1079 cells, the medium was conditioned for 48 hours, while for the BJ fibroblasts, the medium was conditioned for 20 hours. Conditioned media were collected from the cells and fed to a new plate of the same cell type. Control conditioned medium was made by transfecting cells with the same amount of the plasmid that expressed EGFP as was used to transfect the cells with the plasmid that expressed the B18R protein. Luciferase mRNA was transfected into the cells at a final concentration of 1.4 µg/ml in the presence of the conditioned medium, and cells were assayed for luciferase activity 24 hours later according to the procedures described above. Mock transfections with only the transfection reagent without any luciferase mRNA present were done as controls.

Assays for Effects of B18R mRNA on Luciferase Expression

Figure 3:
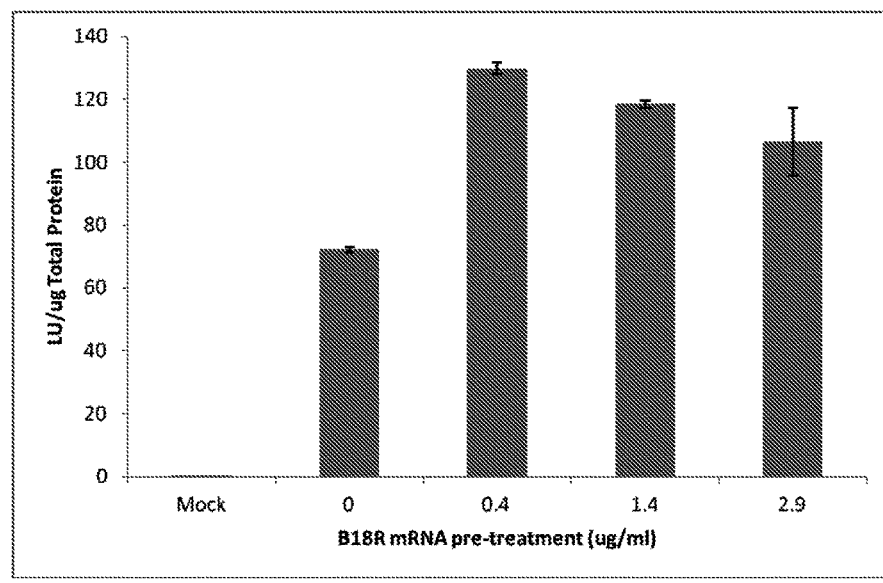
FIG. 3 shows that introduction of an Agent mRNA comprising B18R mRNA boosts expression of Exogenous firefly luciferase (luc2) mRNA. A) 1079 fibroblasts were first transfected with the indicated amount of an Agent mRNA comprising B18R mRNA. Then, after 18 to 20 hours, Exogenous firefly luciferase mRNA was co-transfected along with an additional 1 µg of the Agent mRNA comprising B18R mRNA. Cells were lysed and luciferase assays were performed 20 hours after luciferase mRNA transfections. Mock transfected cells were only treated with the transfection reagent without Exogenous mRNA. B) Similar experiments were performed with a BJ fibroblast cell line, except that the additional Agent mRNA comprising B18R mRNA was omitted from the transfections with Exogenous mRNA comprising luciferase mRNA.
Figure 3:
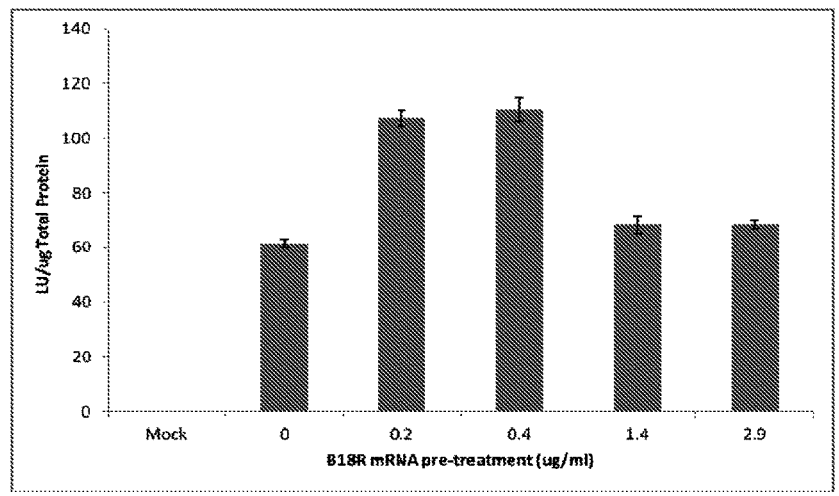

Either BJ or 1079 fibroblast cells were plated at 1×10$^5$ cells per well in a E-well dish coated with 0.1% gelatin. Both cell types were transfected with various amounts of Agent mRNA consisting of B18R mRNA as indicated in FIG. 3 using the procedure described above. After 18 to 20 hours, cells were transfected with luciferase mRNA at a final concentration of 1.4 µg/ml. For 1079 cells, 1 µg of B18R mRNA was also added as a co-transfectant. However, since the additional co-transfection of the 1079 cells with the Agent mRNA consisting of B18R mRNA did not increase luciferase expression compared to the B18R mRNA pre-treatment only, the additional co-transfection was omitted with BJ fibroblast cells and only the pre-treatment with the B18R mRNA was used for the experiment. Cells were lysed and assayed for luciferase activity 20 hours after luciferase mRNA transfection using the procedure described above.

Figure 5:
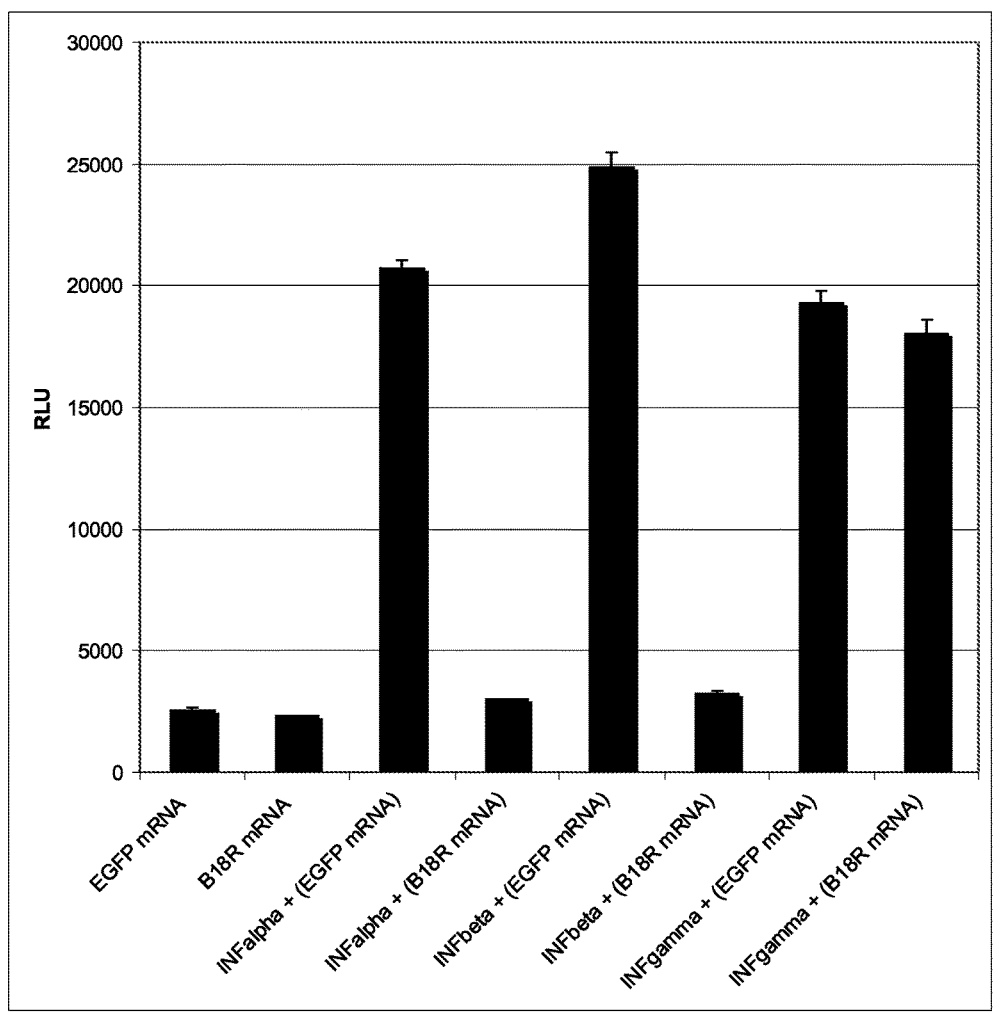
FIG. 5 shows that introducing an Agent mRNA comprising B18R mRNA inhibits type I but not type II interferon activity. An innate immune response reporter Hela cell line with stably integrated Interferon Stimulated Response Elements (ISRE) upstream of firefly luciferase was transfected with an Agent mRNA comprising B18R mRNA (0.5 µg/ml) or a negative control comprising EGFP mRNA (0.5 µg/ml), followed by treatment 8 hours later with recombinant INFα (2777 U/ml), INFβ (333 U/ml) or INFγ (300 ng/ml) proteins. The luciferase assays were performed 16 hours after the addition of recombinant interferons to the cell culture media. In this example, luciferase activity indicates induction of an innate immune response.

Time Course of B18R Pre-Treatment on Expression of Exogenous mRNA 1079 fibroblast cells were plated at 1×10$^5$ cells per well in a 6-well dish coated with 0.1% gelatin. B18R mRNA was transfected at a final concentration of 0.4 µg/ml in fibroblast medium using the procedure described above. At various time points, as indicated in FIG. 5, luciferase mRNA was transfected at a final concentration of 1.4 µgs/ml as described above. Twenty-four hours after luciferase mRNA transfection, cells were lysed as described above for luciferase assays and stored at −80° C. until all time points were collected. Luciferase activity was measured as described above. Mock transfections were done without any luciferase mRNA present in the transfection mixes, and samples were collected after 24 and 48 hours after B18R mRNA transfection.

Use of a Hela Cell Line Containing ISREs to Assay B18R mRNA Inhibition of Specific Interferon Responses In some embodiments, Interferon Stimulated Response Elements (ISRE) (e.g., DNA containing four ISRE sites that exhibit the following sequence (SEQ ID NO:1):

5'-CAGTTTCACTTTCCCCAGTTTCACTTTCCCCAGTTTCACTTTCCC CAGTTTCACTT-3' are inserted into the XhoI and BglII sites of pGL4.26 plasmid (Promega, Madison, Wis.) upstream of a minimal promoter and the luc2 luciferase gene.

In some experiments, a human or animal cell line (e.g., a Hela human cell line) containing the ISREs is generated by using Lipofectamine™ 2000 (Invitrogen, Carlsbad, Calif.) to transfect the cells (e.g., standard Hela cells from ATCC, Manassas, Va.) with the pGL4.264×ISREs-luc2-containing plasmid and clones in which the ISREs-luc2 are integrated are isolated by serial dilution of cells in 96-well dishes and selection with Hygromycin B (InivoGen, San Diego, Calif.; e.g., at 200 µg/ml), followed by confirmation that the cell lines are responsive to recombinant Interferons (e.g., INFα cat #11100-1, INFβ cat#11415-1, and INFγ cat#285-IF from R&D Systems, Minneapolis, Minn.).

The ISREs-luc2 cell line is then used to assay the interferon response that results from the various interferons following transfection of the cell line with Agent B18R mRNA, compared to the interferon response that results following transfection of the cell line with EGFP mRNA as a negative control for the Agent mRNA comprising B18R mRNA. These results indicate if and to what extent the Agent B18R mRNA inhibits or reduces the interferon response by each of the respective interferons (e.g., INFα, INFβ or INFγ), thereby showing the specificity of interferon responses and their levels of response at various times (e.g., 8 hours, 16 hours, 24 hours) after transfection with Agent B18R mRNA compared to the EGFP mRNA as a negative control for the Agent B18R mRNA (e.g., by performing luciferase assays using the Bright-Glo™ Luciferase Assay Reagent from Promega, Madison, Wis., and a SpectraMax M3 luminometer from Molecular Devices, Sunnyvale, Calif.). For example, in some experiments, a Hela line containing the ISREs upstream of the luciferase gene are transfected with B18R mRNA or EGFP mRNA (e.g., each at 0.5 µg-1/ml), followed by treatment 8 hours later with recombinant INFα (2777 U/ml), INFβ (333 U/ml) or INFγ (300 ng/ml) proteins and assay for luciferase activity at various times (e.g., 8 hours, 16 hours, 24 hours, or 48 hours) after the addition of the recombinant interferons to the cell culture media.

Use of a Hela Cell Line Containing ISREs to Assay E3L mRNA Inhibition of Specific Interferon Responses The ISRE-luc2 Hela cell line was also used to test the effect of an Agent mRNA comprising E3L mRNA on the induction of an innate immune response by co-transfected LIN28 dsRNA. The LIN28 coding sequence was cloned in a pUC29-based plasmid downstream of T7 and T3 RNA polymerase promoters, and then different aliquots of the plasmid, which were linearized with BamHI or EcoRI, respectively, were used as templates for in vitro transcription with T7 and T3 RNA polymerases, respectively, in standard in vitro transcription reactions using GAUC canonical NTPs. These complementary RNAs were hybridized to generate dsRNA using the following hybridization parameters; 10 minutes at 70° C., 10 minutes at 60° C., 10 minutes at 50° C., 10 minutes at 40° C., then allowing the RNA to anneal for another 30 minutes at room temperature (22° C.). RNAiMax™ (Invitrogen) was used to transfect ISRE-luc2 cells with 0.2 n/ml of LIN28 dsRNA along with 0.5 µg/ml of either Agent mRNA comprising E3L mRNA or human c-MYC mRNA as a negative control for the Agent E3L mRNA. Bright-Glo™ luciferase assays were performed 18 hours post transfection.

Effects of Agent mRNAs Comprising E3L or K3L mRNA on Expression of Exogenous mRNA Comprising Mouse Alkaline Phosphatase mRNA In order to assay for the effects of Agent mRNA on expression of Exogenous mRNA consisting of mouse ALKP mRNA, 0.2 µg/ml of ALKP GAUC mRNA was transfected using RNAiMax into mouse C3H10T1/2 mesenchymal stem cells or 1079 human fibroblasts, either alone or together with 0.5 µg/ml of Agent mRNA comprising EGFP mRNA, E3L mRNA, K3L mRNA, or both E3L mRNA and K3L mRNA (each at 0.5 µg/ml). Cells were lysed and ALKP reporter assays were performed 18 hours post transfection. Absorbance was read on a spectrophotometer at 405 nm as a readout of ALKP activity.

Use of Agents Comprising E3L or K3L mRNA to Facilitate MYOD mRNA-Induced Reprogramming of Mesenchymal Stem Cells to Myoblast Cells Mouse C3H10T1/2 cells (Passage 16) were plated at $2\times10^5$ cells per well of a gelatin-coated 6-well dish and grown overnight in DMEM, 10% FBS, GLUTAMAX, and pen/strep. The next day, the cells were switched to differentiation media (DMEM+2% horse serum, GLUTAMAX, and pen/strep). MYOD mRNAs were in vitro transcribed using the T7 mScript™ Standard mRNA Production System with GAUC nucleotides while E3L, K3L, EGFP mRNAs were all made using the T7 mScript™ RNA Transcription Kit with GAψm$^5$C nucleotides. Cells were transfected with 0.6 µg/ml of the MYOD GAUC mRNA, and an Agent mRNA comprising E3L GAΨm$^5$C mRNA (5 µg/ml), K3L GAΨm$^5$C mRNA (5 µg/ml), or both E3L GAΨm$^5$C mRNA and K3L GAΨm$^5$C mRNA (5 µg/ml of each) using RNAiMax in differentiation media. mRNA was added to a tube containing OptiMEM media with the total volume equaling 60 µl in tube A. 5 µl of RNAiMax was added to tube B for every µg mRNA totaling 60 µl in tube B. Tube A and Tube B were mixed and incubated at room temperature for 15 minutes. After 15 minutes the mRNA/RNAiMax mix was added to 2 ml of differentiation media already on the cells. The media were changed 4 hours post transfection with new differentiation media. Twenty-four hours after the first transfection another MYOD mRNA transfection was administered. The media were again changed 4 hours post transfection. Forty-eight hours after the first transfection, the cells were fixed and immunofluorescence assays were performed to detect Myosin Heavy Chain (MHC) expression, which is a marker for myoblast muscle differentiation.

Immunofluorescence.

C3H10T1/2 cell plates were washed with PBS and fixed in 4% paraformaldehyde in PBS for 30 minutes at room temperature. The cells were then washed 3 times for 5 minutes each wash with PBS followed by three washes in PBS+0.1% Triton X-100. The cells were then blocked in blocking buffer (PBS+0.1% Triton, 2% FBS, and 1% BSA) for 1 hour at room temperature. The cells were then incubated for 2 hours at room temperature with the primary antibody (mouse anti-human MHC Cat#05-716, Millipore, Temecula, Calif.), at a 1:1000 dilution in blocking buffer. After washing 5 times in PBS+0.1% Triton X-100, the C3H10T1/2 cells were incubated for 2 hours with the anti-mouse Alexa Fluor 555 (Cat#4409, Cell Signaling Technology, Danvers, Mass.) at 1:1000 dilutions in blocking buffer. Images were taken on a Nikon TS100F inverted microscope (Nikon, Tokyo, Japan) with a 2-megapixel monochrome digital camera (Nikon) using NIS-elements software (Nikon).

RESULTS

B18R Protein Increased Activity of Firefly Luciferase mRNA in Cells.

BJ fibroblast cells transfected with luciferase mRNA in the presence of varying concentrations of purified recombinant B18R protein showed an increase in luciferase activity compared to cells transfected in the absence of B18R protein in the same medium (FIG. 1). Mock transfected cells, meaning cells treated with transfection reagent alone, showed no luciferase activity. Luciferase activity increased as the concentration of B18R protein increased up to 200 ng/ml. A drop in luciferase activity was seen at a higher B18R concentration of 400 ng/ml. However the level of luciferase activity at 400 ng/ml of B18R protein was still higher than that in cells transfected in the absence of B18R protein.

Luciferase Activity by Luciferase mRNA is Increased in Cells Expressing B18R Protein.

Figure 2:
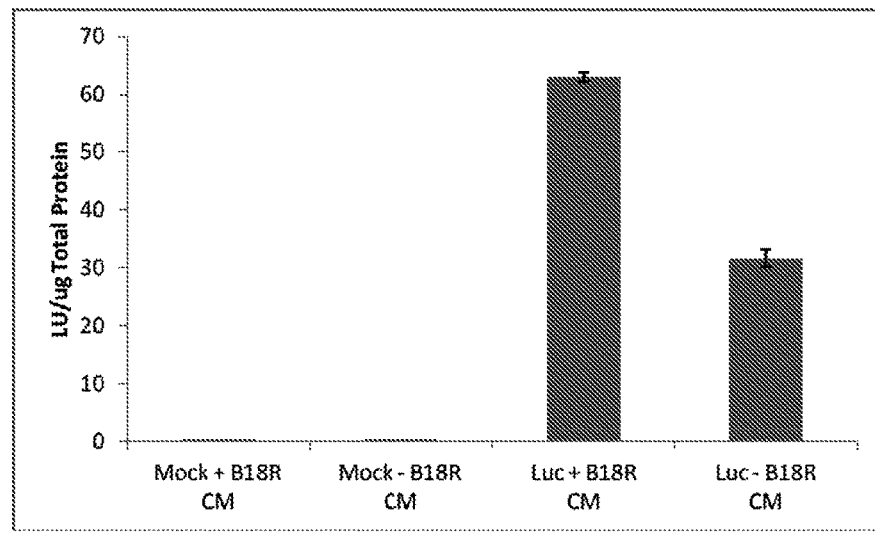
FIG. 2 shows that B18R protein is a secreted factor that increases expression of transfected Exogenous firefly luciferase (luc2) mRNA. A) Medium was conditioned for 48 hours after transfecting 1079 fibroblast cells with a DNA plasmid that expresses B18R protein. Collected conditioned medium (CM) or medium from 1079 fibroblast cells that were not transfected with the DNA plasmid that expresses B18R protein was added to fresh plates of 1079 fibroblast cells, which were then transfected with Exogenous firefly luciferase mRNA. Cells were lysed and luciferase assays were performed 24 hours after the luciferase mRNA transfections. Luciferase activity (LU/µg total protein) is shown for 1079 fibroblast cells that were transfected with the Exogenous luciferase mRNA and then cultured in either B18R-conditioned medium or non-B18R-conditioned medium. Mock-transfected cells were treated with the transfection reagent but without Exogenous luciferase mRNA. B) Similar experiments to those described in A) were performed with a BJ fibroblast cell line. Luciferase activity (LU/µg total protein) was assayed 24 hours after transfecting the BJ fibroblast cells with Exogenous firefly luciferase mRNA in B18R-conditioned medium or non-B18R-conditioned medium.
Figure 2:
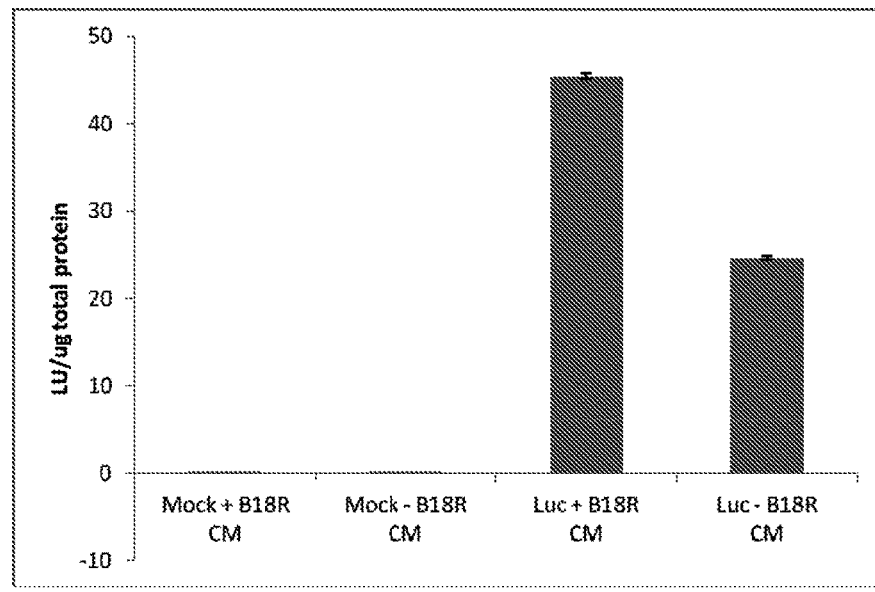

Two cells lines, BJ fibroblasts and 1079 fibroblasts, were tested for the effects of transfecting luciferase mRNA using media conditioned by cells expressing B18R protein. In both BJ fibroblast (FIG. 2 A) and 1079 fibroblast (FIG. 2 B) cell lines, luciferase activity was increased when luciferase mRNA was transfected in the presence of media conditioned by B18R protein-expressing cells compared to cells transfected in media conditioned by EGFP-expressing cells as a negative control. Mock-transfected control cells, which were treated with transfection reagent alone, showed no luciferase activity in either medium.

Introducing B18R mRNA Prior to Transfection of Luciferase mRNA Increased Luciferase Activity.

Transfection of B18R mRNA before transfection of luciferase mRNA increased luciferase activity in both BJ fibroblast (FIG. 3 A) and 1079 fibroblast (FIG. 3 B) cell lines. In 1079 cells, all doses of B18R mRNA transfected 18 to 20 hours prior to luciferase mRNA transfection resulted in an increase in luciferase activity, with the maximal boost seen at the 0.4 µg/ml dose of B18R mRNA (FIG. 3A). BJ fibroblasts also showed an increase in luciferase activity when B18R was transfected into the cells 18 to 20 hours before luciferase transfection (FIG. 3B). At the 1.4 µgs/ml and 2.9 μgs/ml doses of B18R mRNA, the BJ fibroblasts did not have as great of an increase in translation compared to 1079 cells, but this may be due to cell line variations. Mock transfected cells, those treated with transfection reagent only, show no luciferase activity in both cell lines.

Introduction of B18R mRNA Prior to Transfection of Luciferase mRNA Increases Luciferase Activity in Cells.

Figure 4:
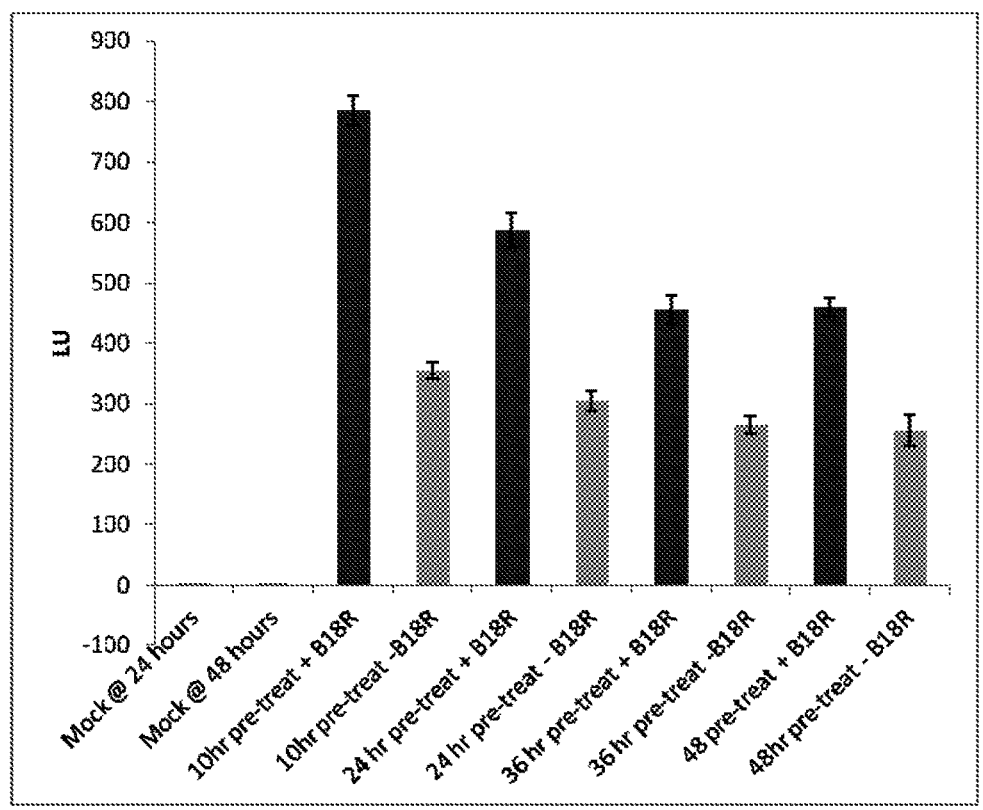
FIG. 4 shows that the optimal length of time for introducing an Agent mRNA comprising B18R mRNA prior to transfection with an Exogenous mRNA comprising firefly luciferase mRNA in order to obtain maximal expression of said Exogenous mRNA is 24 hours or less. 1079 fibroblast cells were grown for various times after introducing to the cells an Agent mRNA comprising B18R mRNA. At various time points after said introducing of the Agent mRNA, the cells were transfected with Exogenous firefly luciferase mRNA or mock transfected with only the transfection reagent, and then the cells were lysed 24 hours later and assayed for luciferase activity (LU/µg total protein). The increase in the expression of the Exogenous mRNA was greatest if the Agent mRNA comprising B18R mRNA was introduced to the cells 24 or less hours prior to the transfection with Exogenous firefly luciferase mRNA. Introducing the B18R mRNA to the cells at a time longer than 24 hours prior to transfecting the cells with the firefly luciferase mRNA did not increase the amount of boost to luciferase activity conferred by the B18R mRNA.

Transfection of B18R mRNA 10, 24, 36, and 48 hours prior to luciferase mRNA transfection increased luciferase activity (FIG. 4). The fold difference between B18R mRNA-treated and un-treated cells was similar at all treatment times, ranging from 1.7- to 2.2-fold, but greatest at the 10-hour treatment time, 2.2-fold change in luciferase activity. There was not an advantage to increasing the time between the B18R mRNA and luciferase mRNA transfections to boost luciferase activity.

Introduction of B18R mRNA into Cells Inhibits Type I but not Type II Interferon Activity.

IFNα, IFNβ and IFNγ have all been shown previously to activate Jak/Stat signaling cascades, ultimately resulting in Interferon Response Factor (IRF) binding to Interferon Stimulated Response Elements (ISREs) eliciting interferon responsive transcriptional activation (Nelson et al., 1993). B18R protein has previously been shown to bind to and inhibit type I interferons (IFNα and IFNβ), but not type II interferons (IFNγ) (Symons et al., 1995). Similarly, based on assays using a Hela cell line that contains ISREs linked to the luc2 gene, B18R mRNA made with ΨTP substituted for UTP (and/or with $m^5$CTP substituted for CTP) results in inhibition IFNα and IFNβ activity, but has no effect on IFNγ activity, whereas other Exogenous mRNAs (e.g., EGFP mRNA as a negative control for Agent mRNA comprising B18R mRNA) does not detectably inhibit the activity of any of the interferons (FIG. 5).

Introduction of E3L or K3L mRNA Prior to Transfection of Alkaline Phosphatase mRNA Increased Alkaline Phosphatase Activity in Cells.

Figure 6:
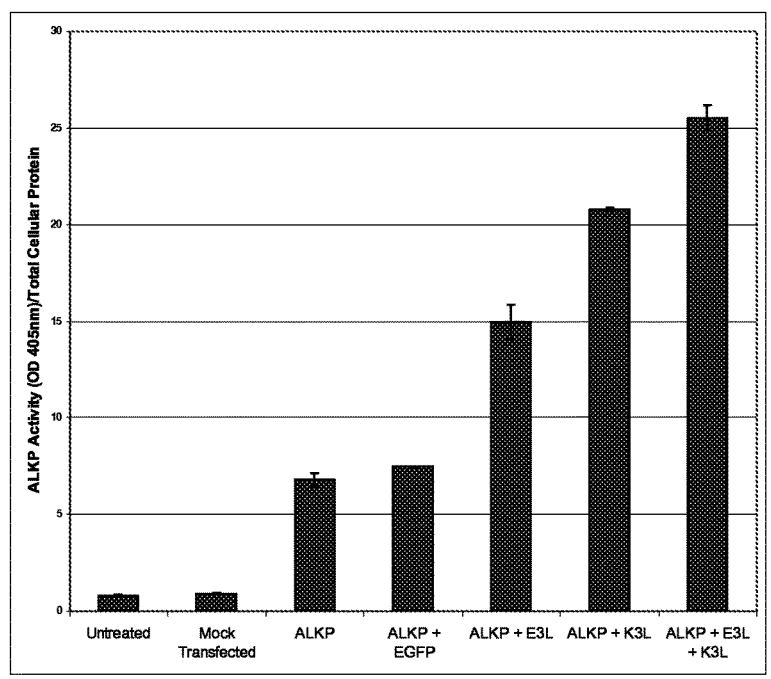
FIG. 6 shows that co-transfection of Agent mRNA comprising either E3L or K3L mRNA (which encode vaccinia virus E3L and K3L protein inhibitors of the interferon innate immune response pathway), enhance activity of an Exogenous mRNA comprising Alkaline Phosphatase (ALKP) reporter mRNA.
Figure 6:
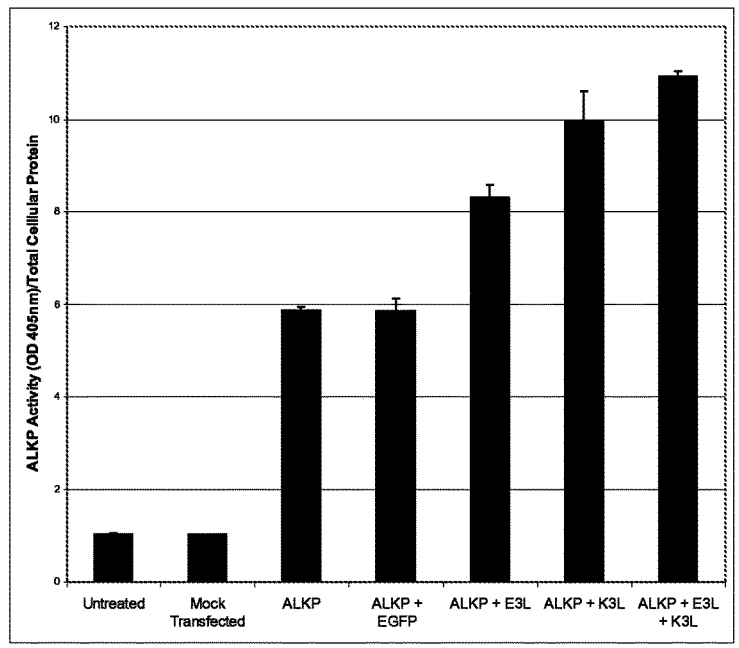

The vaccinia virus E3L and K3L intracellular proteins have been shown to inhibit innate immune system activation elicited by the introduction of dsRNA into the cytoplasm (Carroll et al., 1993; Chang et al., 1992; Davies et al., 1992; Rice et al., 2011; Xiang et al., 2002) Inhibition of the innate immune system by expression of E3L or K3L proteins increases transcription activation by blocking interferon induction through IRF3, the 2-5A/RNaseL pathway, and the PKR pathway (Carroll et al., 1993; Rice et al., 2011; Xiang et al., 2002). Transfection of ALKP mRNA alone or along with EGFP mRNA as a negative control for Agent mRNA comprising E3L or K3L mRNA results in similar ALKP reporter activity in C3H10T1/2 mouse mesenchymal stem cells (FIG. 6A) and 1079 human fibroblasts (FIG. 6B), whereas transfection of ALKP mRNA along with either E3L or K3L mRNAs resulted in significant increases in ALKP reporter activity compared to ALKP mRNA alone. Transfecting both E3L mRNA and K3L mRNA together with ALKP mRNA resulted in an even higher ALKP reporter activity than the affect observed when adding either E3L mRNA or K3L mRNA alone. It is interesting to note that co-transfection of E3L and/or K3L mRNAs with a reporter mRNA (e.g., ALKP mRNA) is sufficient to enhance reporter mRNA translation and activity (FIG. 6). This is not the case with B18R mRNA, which needs to be transfected hours before the reporter mRNA (e.g., luc2 mRNA) is transfected in order to enhance reporter mRNA activity (FIG. 4). E3L and K3L are both intracellular proteins, while B18R is a secreted protein. The delayed effect of B18R mRNA in reducing an innate immune response may be due to the time needed for B18R mRNA to be translated into protein, post-translationally modified, and secreted into the extracellular environment, where it exerts its effect. As shown in FIG. 1, B18R protein can be added directly to media of cells in culture to enhance translation and activity of transfected reporter mRNAs like luciferase mRNA. This shows that secreted proteins that act in the extracellular environment have utility for in vitro cell culture, since these proteins do not need to introduced or internalized into the cells. Intracellular proteins, like E3L and K3L, could be made and purified as recombinant proteins, but the difficulties of introducing such proteins into cells is a major obstacle thereby limiting their utility. Potentially, a variant nucleic acid sequence of an intracellular protein, like E3L or K3L, could be generated using methods disclosed herein so that the protein will have a signal peptide or amino acid sequence which results in uptake or internal localization of the protein into the cell, but making such a variant is also not easy or reliable. However, due to the difficulties of delivering intracellular proteins like the E3L or K3L proteins into cells, the use of an Agent mRNA comprising mRNA that encodes one or both of the E3L and K3L proteins provides clear benefits over the proteins themselves for inhibiting an innate immune response induced in cells by a Foreign Substance (e.g., a LPS, dsRNA or Exogenous RNA).

Introduction of E3L mRNA Inhibits dsRNA-Induced Interferon Stimulation.

Figure 7:
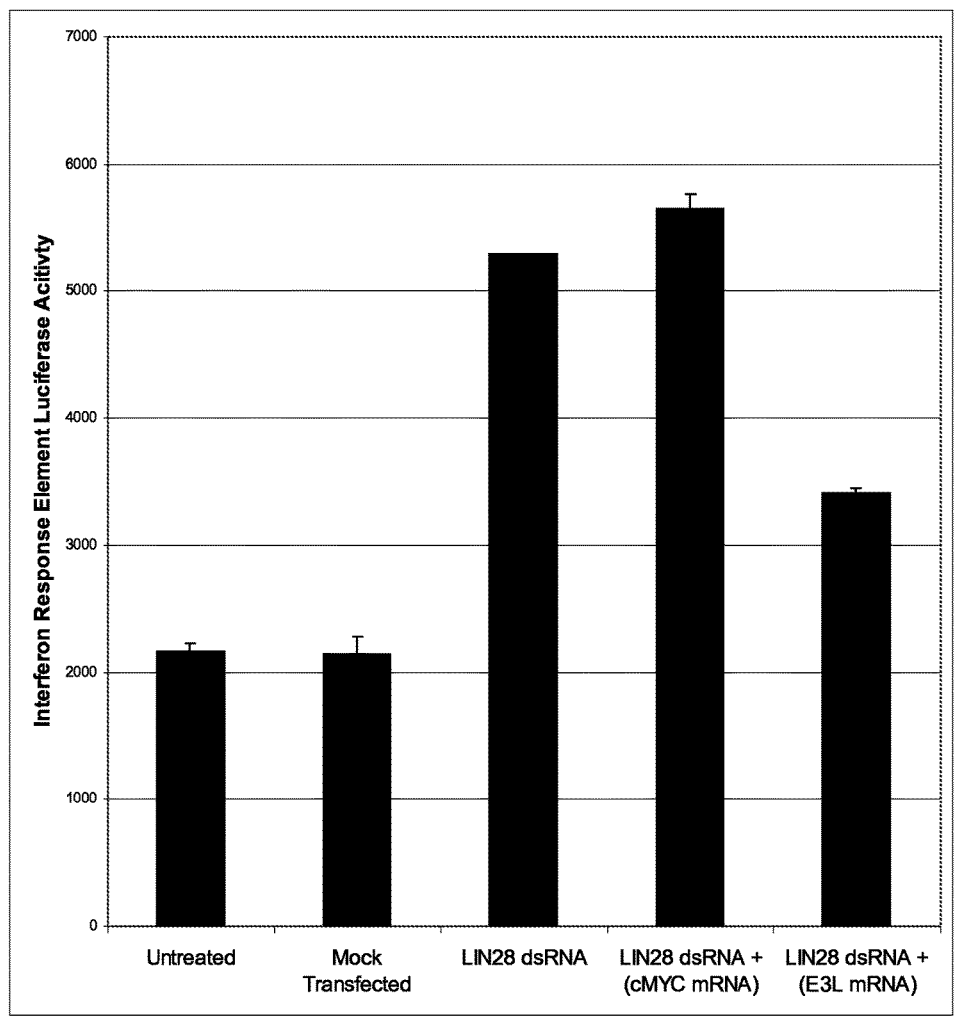
FIG. 7 shows that an Agent mRNA comprising E3L mRNA inhibits dsRNA-induced interferon activity in Hela cells. The ISRE Hela cell line was transfected with 0.2 µg/ml of LIN28 dsRNA alone or together with either 0.5 µg/ml of the Agent mRNA comprising E3L mRNA, or 0.5 µg/ml of cMYC mRNA as a negative control for the Agent mRNA comprising E3L mRNA. Luciferase activity assays (LU/µg total protein) were performed 18 hours post transfection.

Transfection of dsRNA or in vitro transcribed RNA containing unwanted dsRNA contamination is known to bind to Toll-like receptor 3 (TLR3) and activate the immune system resulting in interferon production (Alexopoulou et al., 2001; Kariko et al., 2004). Transfection of dsRNA (e.g., LIN28 dsRNA) into the stable Hela cell line expressing Interferon Stimulated Response Elements (ISRE) driving luciferase 2 expression (ISRE-luc2) resulted in enhanced luciferase reporter activity as a readout of interferon pathway activation (FIG. 7). Transfections of LIN28 dsRNA along with c-MYC mRNA as a negative control for Agent mRNA comprising E3L mRNA does not alter the interferon activation compared to LIN28 dsRNA transfections alone. Transfecting E3L mRNA together with the LIN28 dsRNA substantially reduced the interferon activation compared to transfecting with LIN28 dsRNA alone or co-transfecting with LIN28 dsRNA and c-MYC mRNA.

Introduction of E3L or K3L mRNA into Mesenchymal Stem Cells Facilitates Their Reprogramming to Myoblasts by MYOD mRNA.

Figure 8:
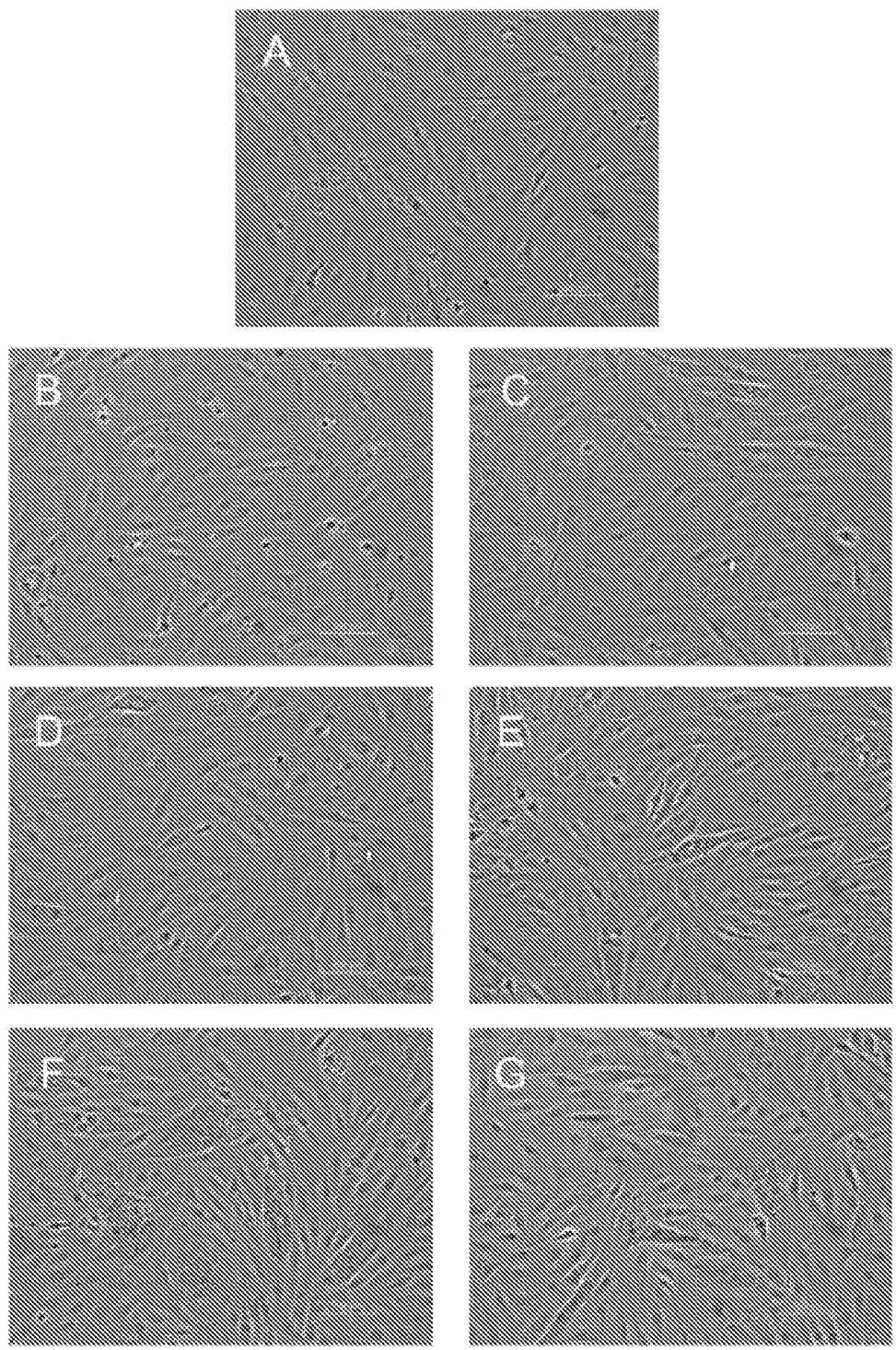
FIG. 8 shows that myoblasts were induced from C3H10T1/2 mesenchymal stem cells that were co-transfected once per day for two days with Exogenous RNA comprising MYOD mRNA (0.6 µg/ml) and an Agent mRNA comprising E3L mRNA (5 µg/ml), K3L mRNA (5 µg/ml), or both E3L mRNA and K3L mRNA (0.5 µg/ml of each), as shown by the Red immunofluorescence staining for Myosin Heavy Chain (MHC), a marker of muscle differentiation, in Panels E, F and G.

Mouse mesenchymal stem cells can be induced to form muscle myoblasts by overexpression of the master regulatory transcription factor, MYOD (Davis et al., 1987). Myoblast induction results in the formation of multinucleated myoblasts expressing myosin heavy chain (MHC) as a marker of muscle differentiation (Davis et al., 1987). We found that MYOD mRNA containing canonical nucleosides (GAUC) could not reprogram C3H10T1/2 mesenchymal stem cells into myoblasts after two successive transfections (FIG. 8.C), including wherein the cells were co-transfected with both MYOD mRNA and EGFP mRNA as a control for Agent mRNA comprising E3L mRNA or K3L mRNA (FIG. 8.D). However, myoblasts were induced when the C3H10T1/2 mesenchymal stem cells were co-transfected with MYOD mRNA (GAUC) together with: E3L mRNA (GAΨ$m^5$C) (FIG. 8.E), K3L mRNA (GAΨ$m^5$C) (FIG. 8.F), or both E3L mRNA and K3L mRNA (FIG. 8.G). Co-transfection of MYOD mRNA together with both E3L mRNA and K3L mRNA did not seem to increase reprogramming (based on MHC expression) compared to co-transfection of MYOD mRNA with either E3L mRNA or K3L mRNA alone (FIG. 8.G versus FIG. 8.E or 8.F). As expected, no myoblasts were induced without MYOD mRNA, as shown for the untreated (FIG. 8.A) and mock-transfected (FIG. 8.B) C3H10T1/2 cells.

Introduction of E3L or K3L mRNA into Human or Mouse Fibroblasts or Keratinocytes Facilitates their Reprogramming to iPS Cells Human or mouse fibroblasts or keratinocytes that are transfected daily for 18 days (at a total daily combined dose of 0.6-1.2 µg (preferably 1-1.2 µg) for all Exogenous mRNA (comprising a 3:1:1:1:1:1 molar ratio of GAψC mRNAs encoding OCT3/4, SOX2, KLF4, NANOG, LIN28 and one protein selected from c-MYC(T58A), c-MYC and L-MYC) per approximately $10^5$ cells) in the presence of E3L GAΨm$^5$C mRNA (5 µg/ml), K3L GAΨm$^5$C mRNA (5 µg/ml), or both E3L GAΨm$^5$C mRNA and K3L GAΨm$^5$C mRNA (5 µg/ml of each) complexed with RNAiMax transfection reagent would result in induction of a higher number of iPS cells compared to the same cells that are similarly transfected with the same Exogenous mRNA in the absent of the Agent mRNA. Thus, Agent mRNA comprising E3L GAΨm$^5$C mRNA and/or K3L GAΨm$^5$C mRNA can increase iPSC induction. Without being bound by theory, it is believed that this increased level of iPSC induction is due to a reduction in the innate immune response and/or an increase in the translation of the Exogenous mRNAs during the reprogramming period.

REFERENCES

Alexopoulou, L., Holt, A. C., Medzhitov, R., and Flavell, R. A. (2001). Recognition of double-stranded RNA and activation of NF-kappaB by Toll-like receptor 3. Nature 413, 732-738.

Andrews-Pfannkoch, C., Fadrosh, D. W., Thorpe, J., and Williamson, S. J. (2010). Hydroxyapatite-mediated separation of double-stranded DNA, single-stranded DNA, and RNA genomes from natural viral assemblages. Appl Environ Microbiol 76, 5039-5045.

Angel, M., and Yanik, M. F. (2010). Innate immune suppression enables frequent transfection with RNA encoding reprogramming proteins. PLoS One 5, e11756.

Barber, R. (1966). The chromatographic separation of ribonucleic acids. Biochim Biophys Acta 114, 422-424.

Beattie, E., Tartaglia, J., and Paoletti, E. (1991). Vaccinia virus-encoded eIF-2 alpha homolog abrogates the antiviral effect of interferon. Virology 183, 419-422.

Carroll, K., Elroy-Stein, O., Moss, B., and Jagus, R. (1993). Recombinant vaccinia virus K3L gene product prevents activation of double-stranded RNA-dependent, initiation factor 2 alpha-specific protein kinase. J Biol Chem 268, 12837-12842.

Carter, P., Bedouelle, H., and Winter, G. (1985). Improved oligonucleotide site-directed mutagenesis using M13 vectors. Nucleic Acids Res 13, 4431-4443.

Cazenave, C., and Uhlenbeck, O. C. (1994). RNA template-directed RNA synthesis by T7 RNA polymerase. Proc Natl Acad Sci USA 91, 6972-6976.

Chang, H. W., Watson, J. C., and Jacobs, B. L. (1992). The E3L gene of vaccinia virus encodes an inhibitor of the interferon-induced, double-stranded RNA-dependent protein kinase. Proc Natl Acad Sci USA 89, 4825-4829.

Clawson, G. A., and Smuckler, E. A. (1982). Increased amounts of double-stranded RNA in the cytoplasm of rat liver following treatment with carcinogens. Cancer Res 42, 3228-3231.

Colamonici, O. R., Domanski, P., Sweitzer, S. M., Lamer, A., and Buller, R. M. (1995). Vaccinia virus B18R gene encodes a type I interferon-binding protein that blocks interferon alpha transmembrane signaling. J Biol Chem 270, 15974-15978.

Davies, M. V., Elroy-Stein, O., Jagus, R., Moss, B., and Kaufman, R. J. (1992). The vaccinia virus K3L gene product potentiates translation by inhibiting double-stranded-RNA-activated protein kinase and phosphorylation of the alpha subunit of eukaryotic initiation factor 2. J Virol 66, 1943-1950.

Davis, R. L., Weintraub, H., and Lassar, A. B. (1987). Expression of a single transfected cDNA converts fibroblasts to myoblasts. Cell 51, 987-1000.

Diebold, S. S., Kaisho, T., Hemmi, H., Akira, S., and Reis e Sousa, C. (2004). Innate antiviral responses by means of TLR7-mediated recognition of single-stranded RNA. Science 303, 1529-1531.

Easton, L. E., Shibata, Y., and Lukaysky, P. J. (2010). Rapid, nondenaturing RNA purification using weak anion-exchange fast performance liquid chromatography. RNA 16, 647-653.

Franklin, R. M. (1966). Purification and properties of the replicative intermediate of the RNA bacteriophage R17. Proc Natl Acad Sci USA 55, 1504-1511.

Gjerde, D. T., Hoang, L., and Hornby, D. (2009). RNA purification and analysis: sample preparation, extraction, chromatography (Weinheim, Wiley-VCH).

Heil, F., Hemmi, H., Hochrein, H., Ampenberger, F., Kirschning, C., Akira, S., Lipford, G., Wagner, H., and Bauer, S. (2004). Species-specific recognition of single-stranded RNA via toll-like receptor 7 and 8. Science 303, 1526-1529.

Hemmi, H., Kaisho, T., Takeuchi, O., Sato, S., Sanjo, H., Hoshino, K., Horiuchi, T., Tomizawa, H., Takeda, K., and Akira, S. (2002). Small anti-viral compounds activate immune cells via the TLR7 MyD88-dependent signaling pathway. Nat Immunol 3, 196-200.

Hemmi, H., Takeuchi, O., Kawai, T., Kaisho, T., Sato, S., Sanjo, H., Matsumoto, M., Hoshino, K., Wagner, H., Takeda, K., et al. (2000). A Toll-like receptor recognizes bacterial DNA. Nature 408, 740-745.

Isaacs, A., and Lindenmann, J. (1957). Virus interference. I. The interferon. Proc R Soc Lond B Biol Sci 147, 258-267.

Judge, A., and MacLachlan, I. (2008). Overcoming the innate immune response to small interfering RNA. Hum Gene Ther 19, 111-124.

Kariko, K., Ni, H., Capodici, J., Lamphier, M., and Weissman, D. (2004). mRNA is an endogenous ligand for Toll-like receptor 3. J Biol Chem 279, 12542-12550.

Kunkel, T. A. (1985). Rapid and efficient site-specific mutagenesis without phenotypic selection. Proc Natl Acad Sci USA 82, 488-492.

Levraud, J. P., Boudinot, P., Colin, I., Benmansour, A., Peyrieras, N., Herbomel, P., and Lutfalla, G. (2007). Identification of the zebrafish IFN receptor: implications for the origin of the vertebrate IFN system. J Immunol 178, 4385-4394.

Lewandowski, L. J., Kimball, P. C., and Knight, C. A. (1971). Separation of the infectious ribonucleic acid of potato spindle tuber virus from double-stranded ribonucleic acid of plant tissue extracts. J Virol 8, 809-812.

Mellits, K. H., Pe'ery, T., Manche, L., Robertson, H. D., and Mathews, M. B. (1990). Removal of double-stranded contaminants from RNA transcripts: synthesis of adenovirus VA RNAI from a T7 vector. Nucleic Acids Res 18, 5401-5406.

Muller, U., Steinhoff, U., Reis, L. F., Hemmi, S., Pavlovic, J., Zinkernagel, R. M., and Aguet, M. (1994). Functional role of type I and type II interferons in antiviral defense. Science 264, 1918-1921.

Nelson, N., Marks, M. S., Driggers, P. H., and Ozato, K. (1993). Interferon consensus sequence-binding protein, a member of the interferon regulatory factor family, suppresses interferon-induced gene transcription. Mol Cell Biol 13, 588-599.

Pays, E. (1977). Characterization of double-stranded ribonucleic acid sequences present in the initial transcription products of rat liver chromatin. Biochem J 165, 237-245.

Rice, A. D., Turner, P. C., Embury, J. E., Moldawer, L. L., Baker, H. V., and Moyer, R. W. (2011). Roles of vaccinia virus genes E3L and K3L and host genes PKR and RNase L during intratracheal infection of C57BL/6 mice. J Virol 85, 550-567.

Schulz, O., Diebold, S. S., Chen, M., Naslund, T. I., Nolte, M. A., Alexopoulou, L., Azuma, Y. T., Flavell, R. A., Liljestrom, P., and Reis e Sousa, C. (2005). Toll-like receptor 3 promotes cross-priming to virus-infected cells. Nature 433, 887-892.

Symons, J. A., Alcami, A., and Smith, G. L. (1995). Vaccinia virus encodes a soluble type I interferon receptor of novel structure and broad species specificity. Cell 81, 551-560.

Triana-Alonso, F. J., Dabrowski, M., Wadzack, J., and Nierhaus, K. H. (1995). Self-coded 3'-extension of run-off transcripts produces aberrant products during in vitro transcription with T7 RNA polymerase. J Biol Chem 270, 6298-6307.

Vallette, F., Mege, E., Reiss, A., and Adesnik, M. (1989). Construction of mutant and chimeric genes using the polymerase chain reaction. Nucleic Acids Res 17, 723-733.

Wang, T., Town, T., Alexopoulou, L., Anderson, J. F., Fikrig, E., and Flavell, R. A. (2004). Toll-like receptor 3 mediates West Nile virus entry into the brain causing lethal encephalitis. Nat Med 10, 1366-1373.

Warren, L., Manos, P. D., Ahfeldt, T., Loh, Y. H., Li, H., Lau, F., Ebina, W., Mandal, P. K., Smith, Z. D., Meissner, A., et al. (2010). Highly efficient reprogramming to pluripotency and directed differentiation of human cells with synthetic modified mRNA. Cell Stem Cell 7, 618-630.

Wells, J. A., Vasser, M., and Powers, D. B. (1985). Cassette mutagenesis: an efficient method for generation of multiple mutations at defined sites. Gene 34, 315-323.

Xiang, Y., Condit, R. C., Vijaysri, S., Jacobs, B., Williams, B. R., and Silverman, R. H. (2002). Blockade of interferon induction and action by the E3L double-stranded RNA binding proteins of vaccinia virus. J Virol 76, 5251-5259.

Zelcer, A., Weaber, K. F., Balazs, E., and Zaitlin, M. (1981). The detection and characterization of viral-related double-stranded RNAs in tobacco mosaic virus-infected plants. Virology 113, 417-427.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method for increasing the translation of a protein or proteins of interest comprising:
    a) introducing in vitro-synthesized Agent mRNA and in vitro-synthesized Exogenous mRNA into a human or animal cell,
    wherein said in vitro-synthesized Exogenous mRNA comprises a protein coding region encoding a protein of interest that is not an innate immune response inhibitor,
    wherein said in vitro-synthesized Agent mRNA comprises: i) mRNA that encodes Vaccinia virus E3L protein, ii) mRNA that encodes Vaccinia virus K3L protein, and iii) mRNA that encodes Vaccinia virus B18R protein, and
    b) culturing said cell under conditions such that said in vitro-synthesized Exogenous mRNA is translated in said cell at an increased level as compared to the level that would be translated in said cell in the absence of said in vitro-synthesized Agent mRNA.

2. The method of claim 1, wherein said cell is an antigen-presenting cell selected from a dendritic cell, a macrophage, a Langerhans cell, a Kuppfer cell, and an artificial APC, from a human or animal patient.

3. The method of claim 1, wherein said introducing results in a corresponding increase in survival of the cell compared to cell survival in the absence of said in vitro-synthesized Agent mRNA.

4. The method of claim 1, wherein said in vitro-synthesized Exogenous mRNA encodes a protein that is able to replace a defective or lacking protein in a cell of a human or animal patient that has an error of metabolism.

5. The method of claim 1, wherein, prior to said introducing, said in vitro-synthesized Agent mRNA or said in vitro-synthesized Exogenous RNA is purified by removing contaminants that are toxic to the cells, wherein the step of purifying is selected from the group consisting of:
    purification performed by HPLC;
    purification using a polymeric resin substrate comprising a C18 derivatized styrene-divinylbenzene copolymer and a triethylamine acetate (TEAA) ion pairing agent in a column buffer along with an acetonitrile gradient;
    purification carried out in a non-denaturing mode;
    purification carried out in a partially denaturing mode;
    purification carried out in a denaturing mode;
    a three-step purification comprising a 8% polyacrylamide gel electrophoresis in 7M urea under denaturing conditions and nondenaturing conditions, further purification using cellulose CF-11 column using an ethanol-salt buffer mobile phase and final purification step using cellulose chromatography;
    purification using an hydroxylapatite (HAP) column under non-denaturing conditions or at higher temperatures;
    purification by weak anion exchange liquid chromatography under non-denaturing conditions; and
    purification comprising treating the in vitro-synthesized Exogenous mRNA and/or said in vitro-synthesized Agent mRNA with an enzyme, wherein said enzyme is ribonuclease III (RNase III) or another enzyme capable of digesting dsRNA greater than twelve basepairs into shorter dsRNA fragments.

6. The method of claim 1, wherein said protein coding region of said in vitro-synthesized Exogenous mRNA encodes one or more transcription factors selected from the group consisting of: OCT3/4, SOX2, KLF4, c-MYC, c-MYC(T58A), L-MYC, NANOG, and LIN28.

7. The method of claim 1, wherein said protein coding region of said in vitro-synthesized Exogenous mRNA is synthesized from only canonical nucleoside-5'-triphosphates selected from: GTP, ATP, UTP, and CTP.

8. The method of claim 1, wherein said protein coding region of said in vitro-synthesized Exogenous mRNA is synthesized using at least one modified nucleotide selected from pseudouridine-5'-triphosphate ($\psi$TP) and 5-methylcytidine-5'-triphosphate ($m^5$CTP).

9. The method of claim 1, wherein said in vitro-synthesized Exogenous mRNA comprises a cap on its 5'-terminus and a poly(A) tail on its 3'-terminus.

10. The method of claim 1, wherein said in vitro-synthesized Agent mRNA and said in vitro-synthesized Exogenous mRNA are introduced into the cell at, or approximately at, the same time.

* * * * *